US009180108B2

(12) United States Patent
Schmitz et al.

(10) Patent No.: US 9,180,108 B2
(45) Date of Patent: Nov. 10, 2015

(54) BACLOFEN FORMULATIONS AND METHODS FOR MAKING SAME

(71) Applicant: Medtronic, Inc., Minneapolis, MN (US)

(72) Inventors: Michael C. Schmitz, Prior Lake, MN (US); Corinne Dominguez, Tolochenaz (CH); Thomas E. Keene, Golden Valley, MN (US); Deanna S. Lane, Golden Valley, MN (US); Lanchi T. Le, Lake Elmo, MN (US); Jianwei Li, Woodbury, MN (US); Ngoc T. Lu, Maple Grove, MN (US); Carmen E. Snaza, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 488 days.

(21) Appl. No.: 13/661,800

(22) Filed: Oct. 26, 2012

(65) Prior Publication Data
US 2013/0109755 A1    May 2, 2013

Related U.S. Application Data

(60) Provisional application No. 61/552,164, filed on Oct. 27, 2011.

(51) Int. Cl.
*A61K 31/197* (2006.01)
*A61K 9/08* (2006.01)
(Continued)

(52) U.S. Cl.
CPC .............. *A61K 31/197* (2013.01); *A61K 9/0085* (2013.01); *A61K 9/08* (2013.01); *A61K 9/0019* (2013.01)

(58) Field of Classification Search
CPC . A61K 31/197; A61K 9/0019; A61K 9/0085; A61K 9/08; A61L 2/07; A61P 21/02; A61P 25/00

USPC .......................................................... 514/567
See application file for complete search history.

(56) References Cited

U.S. PATENT DOCUMENTS 7,824,697 B2    11/2010   Trissel et al.
2005/0079137 A1   4/2005   Blondino et al.
(Continued)

FOREIGN PATENT DOCUMENTS

WO      2008157288 A2    12/2008
WO      WO2010090765   *  8/2010 ........... A61K 31/137

OTHER PUBLICATIONS

Sigg, et al., "Solubilitiy and Stability of Intrathecal Baclofen Solutions at High Concentrations: Implications for Chronic Use in the SynchroMed Infusion System", White Paper, Available through Medtronic, UC200701657B EN NP7533B, 2012.
(Continued)

*Primary Examiner* — Savitha Rao
(74) *Attorney, Agent, or Firm* — William D. Schmidt; Sorell, Lenna & Schmidt LLP

(57) ABSTRACT

Methods for preparing sterilized baclofen solutions include adjusting the pH to below a desired pH, and steam sterilizing the solution with adjusted pH, which results in the solution having the desired pH. Such solutions may also have low concentrations of 4-CPP. Injectable baclofen solutions having greater than 2 mg/mL baclofen include between 5 mM and 25 mM of a phosphate or sulfate species. The solution has an ionic strength equivalent of about 1.5 M NaCl. The present application also provides baclofen formulations for use in treating spasticity, brain injury, cerebral palsy, spinal cord injury, cervical injury, multiple sclerosis, thoracic injury, or withdrawal symptoms.

34 Claims, 24 Drawing Sheets

(51) Int. Cl.
*A61L 2/07* (2006.01)
*A61P 21/02* (2006.01)
*A61K 9/00* (2006.01)

(56) References Cited

U.S. PATENT DOCUMENTS

| | | |
|---|---|---|
| 2006/0009523 A1 | 1/2006 | Trissel |
| 2006/0058221 A1 | 3/2006 | Miller |
| 2008/0182904 A1 | 7/2008 | Ameisen |
| 2008/0206332 A1 | 8/2008 | Kidney et al. |
| 2009/0197958 A1 | 8/2009 | Sastry et al. |
| 2009/0208554 A1 | 8/2009 | Hobot et al. |
| 2010/0137442 A2 | 6/2010 | Sastry et al. |
| 2010/0216887 A1 | 8/2010 | Foster et al. |
| 2010/0255093 A1 | 10/2010 | Edgren et al. |
| 2011/0021437 A1 | 1/2011 | Ellis et al. |
| 2011/0021469 A1 | 1/2011 | Meythaler et al. |
| 2011/0091542 A1 | 4/2011 | Navon et al. |
| 2011/0105614 A1 | 5/2011 | Trissel et al. |
| 2011/0200671 A1 | 8/2011 | Dharmadhikari et al. |
| 2011/0269836 A1 | 11/2011 | Foster et al. |
| 2012/0029230 A1 | 2/2012 | Kuo et al. |
| 2012/0065268 A1 | 3/2012 | Trissel et al. |

OTHER PUBLICATIONS

Albright, et al., "Intrathecal L-baclofen for Cerebral Spasticity: Case Report", Neurology 45, Nov. 1995, pp. 2110-2111.

* cited by examiner

BACLOFEN FORMULATIONS AND METHODS FOR MAKING SAME

CROSS REFERENCE TO RELATED APPLICATIONS

This application claims priority from U.S. Provisional Application Ser. No. 61/552,164, filed on Oct. 27, 2011, the entire contents of which are incorporated herein by reference into the present application.

FIELD

This application relates to, among other things, formulations containing baclofen that are stable in, compatible with, and deliverable via an infusion device.

BACKGROUND

Baclofen is a skeletal muscle relaxant and antispastic agent. Baclofen is a structural analog of the inhibitory neurotransmitter gamma-aminobutyric acid (GABA), and may exert its effects by stimulation of the $GABA_B$ receptor subtype.

Lioresal® Intrathecal (baclofen injection) has been developed for chronic intrathecal infusion for the management of severe spasticity. Baclofen can be administered orally, but when injected directly into the intrathecal space of a patient, therapeutically effective intrathecal concentrations are achieved with resultant plasma concentrations 100 times less than those occurring with oral administration. Baclofen injections (Lioresal® Intrathecal, Medtronic, Inc.) are therefore commonly administered intrathecally to manage severe spasticity of spinal cord origin. Presently, baclofen is commercially available for intrathecal injection, as a 0.05 mg/mL solution, a 0.5 mg/mL solution or a 2 mg/mL solution having a pH of 5 to 7 in the following preservative-free formula (Lioresal® Intrathecal): baclofen (0.05 mg, 0.5 mg or 2 mg); sodium chloride (9 mg); water for injection q.s. 1 mL.

The 0.5 mg/mL and 2 mg/mL concentrations have proven to be very effective for delivery via an implantable infusion device, such as Medtronic, Inc.'s SynchroMed II® infusion device, for a number of patients suffering from severe spasticity. Higher concentration solutions are desired to reduce the frequency with which the reservoir of the implantable infusion device needs to be refilled.

However, since the solubility of baclofen in water is limited, aqueous solutions having higher concentrations of baclofen have not yet become commercially available. At higher concentrations, baclofen may not entirely dissolve in aqueous solution, or it may have an unacceptable tendency to precipitate out of solution during storage.

An upper limit on room temperature aqueous solubility of baclofen has been reported by some sources to be about 4 mg/mL, however such a concentration appears to require an equilibrium state in which particulate baclofen is present at some level.

Commercially and pharmaceutically acceptable injectable baclofen solutions for parenteral use or to be delivered via an infusion system desirably will be essentially free from particles that can be observed on visual inspection and the baclofen will stay in solution without precipitating prior to and during administration to a patient.

Recent reports suggest that higher concentrations of baclofen without significant precipitation of particles can be achieved when baclofen is dissolved in hot water and cooled, or baclofen is dissolved in highly acidic or basic solutions and back-titrated towards neutral pH. However, it is desired for injectable baclofen solutions to have no detectable (observable on visual inspection) amount of particulates.

Injectable baclofen solutions will also desirably have a limited amount of degradation products. The main decomposition product of baclofen is 4-(4-chlorophenyl)-2-pyrrolidine (4-CCP). For example, one of the currently available injectable baclofen solution described above (Lioresal® Intrathecal) generally contains about 0.6% of 4-CPP (relative to the starting concentration of baclofen). The rate conversion of baclofen to 4-CPP is known to increase at increased temperatures. Injectable baclofen solutions are desirably sterilized. However, if heat sterilization is used in manufacturing, this may result in an undesirably increased amount of degradation products.

It would therefore be desirable to provide new baclofen formulations and sterilization processes of injectable baclofen formulations that limit the production of 4-CPP.

SUMMARY

New baclofen formulations are provided that contain greater than 2 mg/mL baclofen that are essentially free from particulates that can be observed on visual inspection. Methods that may be used to heat-sterilize baclofen solutions without excessive generation of 4-CPP are also provided.

In one embodiment, baclofen solutions that contain between 5 mM and 25 mM sulfate or phosphate can have concentrations of baclofen greater than 2 mg/mL without detectable particulates, and which remain free of detectable particulates for a period of at least 30 days.

In another embodiment, a method is provided for reducing the pH of a baclofen solution to a pH reducing the pH prior to heat sterilization that results in a solution with low 4-CPP concentrations when the pH is adjusted to the desired ultimate pH after heat sterilization.

In various embodiments, a method is provided for preparing a terminally sterilized injectable baclofen formulation suitable for injection into cerebrospinal fluid of a patient. The method includes (i) dissolving baclofen in an aqueous solvent, selected from water, a saline solution, water containing phosphate, sulfate, potassium or magnesium or a saline solution containing sulfate, phosphate, potassium, or magnesium to generate an initial solution, wherein the concentration of baclofen in the initial solution is between 0.05 mg/mL and 7 mg/mL; (ii) adjusting the pH of the initial solution to between 5.0 and 6.2 to produce a pH adjusted solution; and (iii) steam sterilizing the pH adjusted solution to a sterility assurance level of $1 \times 10^6$, producing a terminally sterilized solution. The terminally sterilized solution, after storage of 30 days (and in some embodiments after 6 months) at room temperature, has a pH of between 5.0 and 7.0 and less than 1.3% of 4-(4-chlorophenyl)-2-pyrrolidinone (4-CPP) based on the concentration of baclofen added to the initial solution. In some embodiments, the terminally sterilized solution, after storage of 30 days at room temperature (and in some embodiments after 6 months), has less than 1% of 4-(4-chlorophenyl)-2-pyrrolidinone (4-CPP) based on the concentration of baclofen added to the initial solution.

In other embodiments, an injectable baclofen solution includes (i) baclofen in a concentration greater than 2 mg/mL; and (ii) sulfate or phosphate in a concentration of between 5 mM and 25 mM. The solution has an ionic strength equivalent of about 1.5 M NaCl (e.g., 1.4 M NaCl to 1.6 M NaCl). In some embodiments, the solution consists of, or consists essentially of, baclofen, the sulfate or phosphate, sodium ion, and water. In other embodiments, the solution consists of, or consists essentially of, baclofen, the sulfate or phosphate, sodium ion, chloride ion and water.

Baclofen prepared in accordance with the methods described herein or having the formulations described herein may be advantageously used with infusion devices such as external infusion pumps and/or implantable infusion pumps.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
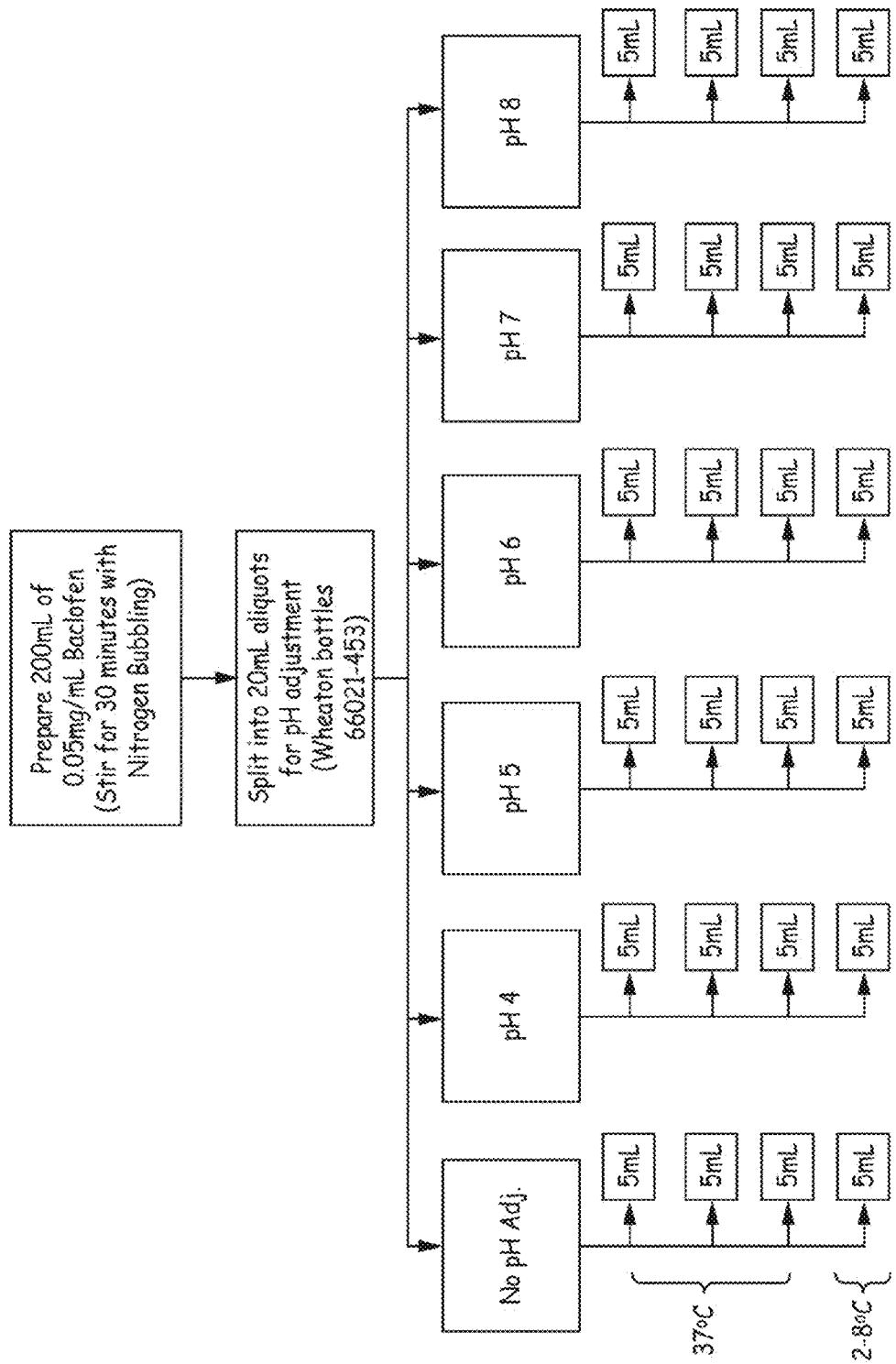
FIG. 1 is a flow diagram illustrating an experimental design employed in an Example presented herein.

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like. For example, an injectable baclofen composition comprising baclofen, sulfate or phosphate, and a cation, such as a sodium ion, or a potassium ion may consist of, or consist essentially of, baclofen, sulfate or phosphate, and a cation, such as a sodium ion or potassium ion.

"Consisting essentially of", as it relates to a compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods. For example, in embodiments, it is desired to produce compositions that are free of detectable particulate matter, such as precipitated baclofen, over time. Accordingly, components or processing steps that result in increased particulate matter may be considered to materially affect the basic and novel properties of the compositions or processes. By way of further example, it is desired, in embodiments, to produce a composition having a pH that remains within a range over time. Accordingly, components or processing steps that result in pH drifting beyond the range may be considered to materially affect the basic and novel properties of the compositions or processes. Other aspects that may be considered to materially affect the basic and novel properties of the compositions, articles, systems, apparatuses or methods described herein will be apparent upon reading the disclosure presented herein. Embodiments of the present disclosure provide formulations containing baclofen for use in an infusion device. Preferably, such formulations are stable in, compatible with, and deliverable by an implantable infusion device.

The formulation containing baclofen may be used in treating or inhibiting disease or injury responsive to baclofen. Illustrative examples of a disease or injury responsive to baclofen include, but are not limited to, spasticity, brain injury, cerebral palsy, spinal cord injury, cervical injury, multiple sclerosis, thoracic injuries, spinal pathology, or combinations thereof. In some embodiments, the formulations containing baclofen may be used as therapy to treat spasticity. In the context of the present disclosure, the terms "treat", "therapy", and the like are meant to include methods to alleviate, slow the progression, prevent, attenuate, or cure the treated disease.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Baclofen

Baclofen as used herein refers to 4-amino-3-(p-chlorophenyl)butyric acid, enantiomers, racemic mixtures, polymorphs, salts, solvates, esters, or hydrates thereof. Baclofen includes R-baclofen (D-baclofen), S-baclofen (L-baclofen), or their mixtures including the racemate. The racemate refers to a mixture of R and S-baclofen (DL-baclofen) in equal proportions. The phrase "pharmaceutically acceptable salt(s)", as used herein, means those salts of compounds of the invention that are safe and effective for use in mammals and that possess the desired biological activity.

Salts of baclofen include salts of acidic or basic groups present in compounds of the application. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, or pamoate salts. Certain compounds of the invention can form pharmaceutically acceptable salts with various amino acids. Suitable base salts include, but are not limited to, aluminum, calcium, lithium, magnesium, potassium, sodium, zinc, or diethanolamine salts. Potassium salts include potassium chloride, potassium bicarbonate, potassium phosphate, gluconate, potassium citrate, or the like.

Baclofen exhibits the following structural formula:

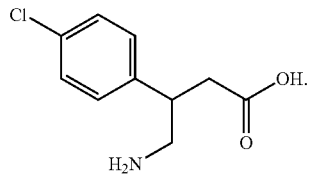 [SMILES: NCC(CC(=O)O)c1ccc(Cl)cc1]

The inventors have found that the R isomer (D) isomer) and racemic mixtures of baclofen (DL-baclofen) behave essentially the same with regard to solubility, stability and pH as related to the present disclosure (data not shown). Accordingly, the Examples presented herein, which employed a racemic mixture, are also applicable to the L-isomer (S-isomer).

Formulation

As used herein, a formulation for use in an implantable or external infusion device comprises a fluid composition. Typically, the formulation comprising baclofen can be used in an implantable infusion device and is a fluid composition at room temperature and at body temperature of the subject in which the formulation is infused. Fluid compositions include solutions, suspensions, dispersions, or the like. Preferably, the fluid composition is a solution that is essentially free or free from particles or particulates that can be observed on visual inspection. The term "particulate" includes mobile undissolved particles, other than gas bubbles, unintentionally present in the drug solution.

While the fluid compositions may contain any of a number of known pharmaceutical additives or excipients, in many embodiments, the fluid compositions contain as few ingredients or components as possible to achieve a desired pH, stability (low 4-CPP), solubility, and tonicity or ionic strength.

Preferably, the fluid composition has a pH of between 5.0 and 7.5, such as between 5.5 and 6.5, or about 6.0. For example, the pH can be about 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

Preferably, the fluid composition has a concentration of 4-CPP of 1.3% or less (based on the starting concentration of baclofen), such as about 1% 4-CPP or less, or about 0.6% 4-CPP or less. For example, in some embodiments, the level of 4-CPP in the terminally sterilized solution is less than about 1.2%, 1.1%, 1.0%, 0.9%, 0.8%, 0.7%, 0.6%, 0.5%, 0.4%, 0.3%, 0.2%, 0.1%, 0.05%, 0.025%, or lower.

In some embodiments, the current application provides a method of reducing formation of 4-(4-chlorophenyl)-2-pyrrolidinone (4-CPP) in a terminally sterilized injectable baclofen formulation, the method comprising: adjusting a pH of baclofen in an aqueous solvent to between about 4.0 and about 6.2 to form a pH adjusted solution, the aqueous solvent comprising water, a saline solution, water containing phosphate, sulfate, potassium, magnesium or a saline solution containing sulfate, phosphate, potassium or magnesium, wherein the concentration of baclofen in the aqueous solvent is between 0.05 mg/mL and 10 mg/mL; and steam sterilizing the pH adjusted solution to achieve a sterility assurance level of $1\times10^6$ so as to form a terminally sterilized solution having a pH of between about 5.0 and about 7.5, the terminally sterilized solution having less than 1.0% of 4-CPP based on the concentration of baclofen added to the aqueous solvent.

In some embodiments, the present application provides methods and baclofen formulations having low 4-CPP concentrations by controlling the pH of the baclofen solution prior to steam sterilization, where the pH is in the range of between about 4.0 to about 7.0, the amount of 4-CPP formed is reduced, when the pH is raised to between about 5.0 to about 7.0 after heat sterilization. In some embodiments, the 4-CPP impurity levels are low at a pH of between about 4.0 to about 4.5. The pH profile of the baclofen, prior to steam sterilization and the 4-CPP impurity levels post-steam sterilization are shown below in Table A.

TABLE A

| pH | Impurity Level of 4-CPP |
|---|---|
| 4.0 | 1.7 |
| 4.2 | 1.3 |
| 4.4 | 1.1 |
| 4.6 | 0.7 |
| 4.8 | 0.5 |
| 5.0 | 0.4 |
| 5.2 | 0.4 |
| 5.4 | 0.5 |
| 5.6 | 0.6 |
| 5.8 | 0.7 |
| 6.0 | 0.8 |
| 6.2 | 0.9 |
| 6.4 | 1.1 |
| 6.6 | 1.2 |
| 6.8 | 1.4 |
| 7.0 | 1.5 |

The formulation may have any suitable ionic strength. The formulation may include a salt, such as NaCl or KCl, to maintain ionic strength. In various embodiments, the combined ionic strength of the formulation contributed by the various components of the formulation, such as baclofen, and one or more salts is the equivalent of the ionic strength of between about 0.1 M and 0.2 M NaCl or KCl, or about 0.15 M NaCl or KCl. For example, 25 mM $Na_3PO_4$ buffer solution may include 0.085M NaCl or KCl to yield a combined ionic strength of the buffer and the NaCl or KCl at an equivalent of 0.15 M NaCl (e.g., about 0.154 M NaCl or KCl), which is substantially isotonic with CSF.

In embodiments where the formulation is to be delivered to a central nervous system of a subject, it may be desirable for the formulation to be isotonic with cerebrospinal fluid, which typically has a tonicity of about 305 mOsm. For purposes of the present disclosure, a formulation having a tonicity of between about 270 mOsm and 315 mOsm, e.g., between about 285 mOsm and 315 mOsm is considered to be isotonic with cerebrospinal fluid. While such tonicities are desired, the overall ionic strength of the formulation may, in many cases, take precedence over the desire to achieve isotonicity.

In various embodiments, injectable baclofen solutions include sulfate or phosphate. As used herein, "sulfate" refers to $SO_4^{2-}$ or $HSO_4^-$. As used herein, "phosphate" refers to $PO_4^{3-}$, $HPO_4^{2-}$, or $H_2PO_4^-$. It will be understood that when in water the various species of sulfate or phosphate will be in equilibrium. When a concentration of sulfate or phosphate is used herein, the concentration will refer to the total concentration of all of the various species of sulfate or phosphate present. Sulfate or phosphate may result from dissolving an appropriate acid or salt of sulfate or phosphate in the solution. In many embodiments, sulfate is derived from $Na_2SO_4$. In embodiments, the phosphate is derived from $NaH_2PO_4$.

It has been found that the solubility of baclofen is increased in solutions comprising sulfate or phosphate. As discussed in more details in the Examples that follow, it has been found that concentrations greater than 2 mg/mL, such as greater than 4 mg/mL, greater than 5 mg/mL, greater than 6 mg/mL, or greater than 7 mg/mL baclofen can be dissolved in solutions containing phosphate, sulfate, potassium, or magnesium.

In some embodiments, the present application provides stable aqueous baclofen solutions at concentrations greater than the 2.0 mg/mL, and methods of preparing such solutions. In particular, in some embodiments, the present application provides stable aqueous baclofen solutions having concentrations greater than about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0 mg/mL.

In some embodiments, the present application provides stable aqueous baclofen solutions having concentrations less than about 7.5, 8.0, 8.5, 9.0, 9.5, 10.0, 10.5, 11.0, 11.5 or 12.0 mg/mL. The term "stable," as used herein, is meant to describe a compound, composition, or other substance that retains its properties without loss of potency and maintains its physical characteristics over time with minimal degradation.

In some embodiments, the concentration of phosphate or sulfate is between 5 mM and 25 mM. At concentrations above 25 mM, the phosphate or sulfate may provide the solution with sufficient ionic strength such that no ionic strength enhancing agent is added to increase the ionic strength. If the resultant solution has an ionic strength less than about 1.5 M NaCl, an ionic strength enhancing agent such as NaCl may be added to produce a suitable ionic strength.

In various embodiments, the fluid composition containing baclofen is an injectable baclofen solution. The solution, in embodiments, includes (i) baclofen in a concentration greater than 2 mg/mL; and (ii) sulfate or phosphate in a concentration of between 5 mM and mM. The solution has an ionic strength equivalent of between 1.4M NaCl and 1.6 M NaCl. In some embodiments, the solution consists essentially of the baclofen, the sulfate (e.g., from $Na_2SO_4$) or phosphate (e.g., from $NaH_2PO_4$), sodium ion, and water. In embodiments, the solution consists essentially of the baclofen, the sulfate or phosphate, sodium ion, chloride ion (e.g., from NaCl), and water.

Preparation

Any appropriate form of baclofen can be used to prepare the formulations of the present application. In some embodiments, appropriate forms of baclofen include baclofen solids such as powdered, lyophilized or microfluidized baclofen. In some embodiments, the baclofen can be provided as aqueous or non-aqueous solutions of baclofen, including buffered solutions, where pharmaceutically undesirable components of the solution are either diluted to pharmaceutically-acceptable levels or removed from the final baclofen formulation prior to pharmaceutical administration. In some embodiments, the baclofen that can be used in the formulation comprises amorphous baclofen.

Fluid compositions comprising baclofen as described herein may be prepared in any suitable manner. Preferably the fluid compositions are sterilized. As used herein, "sterilized" means essentially free or free of microorganisms (e.g., bacteria, viruses, fungi, etc.) and their spores. Often sterility assurances of a $1\times10^6$ reduction are required to claim terminal sterility. In various embodiments the compositions are sterilized by heat treatment, such as steam sterilization or autoclaving. In some embodiments, heat treatment, regardless of temperature, time or type, which results in a $1\times10^6$ sterility assurance level (the probability that a given unit is not sterile is one in a million) is used. In some embodiments, the fluid compositions are sterilized to an $F_0$ for at least 15 minutes at 121° C.

Heat sterilization, however, can result in increased production of 4-CPP. As discussed below in more detail in the Examples that follow, it has been found that adjusting the pH to a pH lower than the ultimate desired pH can result in less 4-CPP production following heat treatment. It has also been found that the pH tends to increase following heat treatment. Accordingly, a baclofen composition may be pH adjusted to a pH less than the ultimately desired pH and then heat sterilized to produce a low 4-CPP composition with a desired long term pH.

In various embodiments, a method for preparing a terminally sterilized injectable baclofen formulation suitable for injection into cerebrospinal fluid of a patient includes (i) dissolving baclofen in aqueous solvent to generate an initial solution, wherein the concentration of baclofen in the initial solution is between 0.05 mg/mL and 7 mg/mL; (ii) adjusting the pH of the initial solution to between 5.0 and 6.2 to produce a pH adjusted solution; and (iii) steam sterilizing the pH adjusted solution to an $F_0$ for at least 15 minutes at 121° C. to produce a terminally sterilized solution, wherein the terminally sterilized solution, after storage of 30 days at room temperature, has a pH of between 5.0 and 7.0 and less than 1.3% of 4-(4-chlorophenyl)-2-pyrrolidinone (4-CPP) based on the concentration of baclofen added to the initial solution. In some embodiments, the terminally sterilized solution, after storage of 30 days at room temperature, has less than about 1% 4-CPP.

In some embodiments, the aqueous solvent is preferably water, a saline solution (which, as used herein, means a solution consisting of or consisting essentially of water and dissolved sodium chloride), a sulfate or phosphate solution (which, as used herein, means a solution consisting of or consisting essentially of water and dissolved sulfate or phosphate salt or acid), or a sulfate or phosphate saline solution (which, as used herein, means a solution consisting of or consisting essentially of water and dissolved sodium chloride and dissolved sulfate or phosphate salt or acid).

The terminally sterilized injectable baclofen formulation may have any suitable concentration of baclofen, such as between 0.01 mg/mL and 10 mg/mL baclofen. In embodiments, the terminally sterilized injectable baclofen formulation has between 0.05 mg/mL and 2 mg/mL baclofen.

The pH may be adjusted with any suitable acid or base. In embodiments, the pH is adjusted with HCl, $H_2SO_4$, $H_3PO_4$ or NaOH.

In embodiments, the terminally sterilized injectable baclofen formulation has an ionic strength equivalent to about 1.4 M NaCl to about 1.6 M NaCl, such as about 1.5M NaCl. NaCl may be added to achieve a desired ionic strength.

In embodiments, the terminally sterilized solution, after storage of 30 days at room temperature, has a pH of between 5.5 and 6.5, such as about 6.0.

In embodiments, the concentration of baclofen in the initial solution is about 0.05 mg/n L, and the pH is adjusted to between 5.0 and 5.5.

In embodiments, the concentration of baclofen in the initial solution is about 0.5 mg/mL, and the pH is adjusted to between 5.5 and 6.2.

In embodiments, the concentration of baclofen in the initial solution is about 2 mg/mL, and the pH is adjusted to between 5.5 and 6.2.

In embodiments, the initial solution consists essentially of baclofen, dissolved NaCl or KCl and water.

Administration

Formulations according to the present disclosure may be administered to a subject through any acceptable route. For example, the fluid formulations may be administered intravenously, subcutaneously, intramuscularly, intra-arterially, inthrathecally, epidurally, intraparenchymally, intraperitoneally, intracerebroventricularly, intaventically, etc., by infusion or injection.

Preferably, a therapeutically effective dose of baclofen is administered to a patient in need of treatment. By "therapeutically effective dose" herein is meant a dose that produces the effects for which it is administered. The exact dose will depend on the purpose of the treatment, and will be ascertainable by one skilled in the art using known techniques. In some embodiments, dosages of about 0.5 micrograms/kg to about 5 micrograms/kg are used. As is known in the art, adjustments for systemic versus localized delivery, and rate of new protease synthesis, as well as the age, body weight, general health, gender, diet, time of administration, drug interaction and the severity of the condition may be necessary, and will be ascertainable with routine experimentation by those skilled in the art.

In some embodiments, baclofen is delivered to a patient in a daily dose of between about 0.001 mg/kg/day to 100 mg/kg/day. A "patient" for the purposes of the present disclosure includes both humans and other animals, particularly mammals including mice, rats, guinea pigs, rabbits, dogs, cats, swine, bovine, monkey, baboon, chimpanzee, and other organisms. Thus, the methods are applicable to both human therapy and veterinary applications. In a preferred embodiment the patient is a mammal, such as a human. Those "in need of treatment" include mammals already having the disease or disorder, as well as those prone to having the disease or disorder, including those in which the disease or disorder is to be prevented.

The baclofen formulations of the current application allows for subsequent dilution by the addition of other components that are to be simultaneously infused with the baclofen. These include pain relieving medications suitable for combination with the baclofen and include morphine, clonidine, hydromorphine, hydrocodone, merperidine, celeroxib, tramadol, oxycodone, acetaminophen, ketoprofen, ketorolac, ibuprofen, naproxen, or the like. It is appreciated in the art that other chemical compounds are similarly suitable for co-administration or separate administration with baclofen in the current application.

The stable baclofen formulations of the present application can be provided in a medical package of baclofen solution suitable for injection. In some embodiments, the medical package contains a solution that is compatible with the desired site of administration (e.g., cerebrospinal fluid suitable for intrathecal administration). In some embodiments, the baclofen formulation will be provided in a sterile, isotonic solution of baclofen free of pyrogens, antioxidants, preservatives or other potentially neurotoxic additives.

The baclofen formulations of the present application can be packaged in a pre-filled syringe that is ready for immediate delivery to an infusion device. The packaging includes a syringe with a leur-lock tip filled with the baclofen, a color coding system (label) for the various concentrations of the drug product and size of syringe, a package, a label, and instructions for use. The term "pre-filled," as used herein, means containing an exact, pre-determined dose of a sterile pharmaceutical composition.

Infusion Device

Any suitable infusion device may be used to deliver the formulation containing baclofen to a patient. The infusion device may include an osmotic pump, a fixed rate or variable rate pump, a piston pump, a peristaltic pump, or the like. Typically, infusion devices include reservoirs for housing the fluid formulation. A catheter is typically connected to the infusion device so that fluid from the reservoir may be pumped from the reservoir through the catheter to a targeted region of the patient. In some embodiments, the infusion device is implantable and includes a microprocessor for controlling the rate of delivery of the formulation, which may be variable. In such embodiments, the implantable infusion device may communicate and receive infusion instructions from an external device, such as a physician programmer device. A suitable infusion device for use with the baclofen formulations of the current application is an implantable infusion device, such as Medtronic, Inc.'s SynchroMed II®.

Baclofen Side Effects

Commonly used baclofen, e.g., Lioresal®, is a racemic mixture of D-baclofen (also known as S-baclofen) and L-baclofen (also known as R-baclofen). The skeletal muscle spasmolytic activity of DL-baclofen exists almost entirely with the L isomer, which has 100 to 1000 times more affinity for the CNS GABA-b receptor, the site of the desired pharmacologic activity of baclofen.

Studies were performed to examine the effects of different baclofen compositions delivered intrathecally to rats. In one study, the therapeutic response mediated by spinal GABA-b receptors (thermal analgesia) with a nonspecific side effect (impaired motor skills on the rotarod) caused by L or DL-baclofen were compared. Equivalent doses of L-baclofen and DL-baclofen (adjusted to deliver the same amount of L-baclofen) produced very similar analgesic activity in the thermal nociception assay, while D-baclofen was ineffective (data not shown). However, L-baclofen caused statistically less motor impairment on the rotarod than DL-baclofen at equivalent doses, while D-baclofen alone had no significant effect (data not shown). These results surprisingly suggest that the combination of the D and L isomers in DL-baclofen may enhance side effects of L baclofen.

We conclude that delivery of L-baclofen alone (i.e., rather than a racemic mixture) may provide equivalent therapy to DL-baclofen with fewer side effects in clinical practice.

In some embodiments, when DL-baclofen is administered for long periods of time (e.g., one month or longer), the patient may have withdrawal symptoms when the drug is discontinued. Such withdrawal symptoms may include hallucinations, seizures, high fever, rebound spasticity, rapid breakdown of muscle tissue, organ failure, low pressure, or other symptoms. It is contemplated that the L-baclofen in DL-baclofen may be responsible for these withdrawal symptoms. Therefore, by reducing the amount of L-baclofen administered, withdrawal symptoms can be reduced. In some embodiments, by reducing the L-baclofen content or by administering pure or substantially pure D-baclofen, the withdrawal symptoms can be reduced or eliminated. Substantially D-baclofen includes that the baclofen is free from other isomer forms. In some embodiments, the D-baclofen is at least 90% free, preferably at least 95% free and, more preferably, at least 99% free of L-baclofen.

In some embodiments, the present application provides a method of reducing or eliminating baclofen withdrawal symptoms in a patient undergoing chronic baclofen treatment (e.g., treatment lasting more than one month) by administering D-baclofen to the patient to reduce or eliminate the baclofen withdrawal symptoms. In some embodiments, the D-baclofen can be administered to replace the chronically administered DL-baclofen so that the patient receives the D-baclofen isomer and then the patient can be titrated off the L-baclofen to reduce or eliminate the baclofen withdrawal symptoms. For example, a patient receiving long term baclofen therapy with the L-baclofen or the DL-baclofen will have withdrawal symptoms, due in part to receiving the L-isomer, by replacing the L-isomer with the D-isomer, the withdrawal symptoms can be reduced and/or eliminated. The exact dose of D-baclofen will depend on the purpose of the treatment, and will be ascertainable by one skilled in the art. In some embodiments, dosages of D-baclofen can be used in an amount of about 0.5 micrograms/kg to about 5 micrograms/kg, which is the usual dose for the D-L baclofen.

Having now generally described the application, the same may be more readily understood through the following reference to the following examples, which are provided by way of illustration and are not intended to limit the present application unless specified.

EXAMPLES

In the following Examples, studies performed and results obtained for determining suitable formulations containing baclofen for use in an infusion device are described.

Example 1

Initial Studies on Effect of Heat Sterilization on Baclofen Solutions

The initial studies were designed to determine methods to obtain terminally sterilized injectable baclofen solutions having a final pH of between 5.0 and 7.0 with the degradant 4-CPP (4-4-Chlorophenyl)-2-pyrrolidinone) being present in less or equal to 1.3% of the total weight of initial baclofen (the "Release Specifications").

Isotonic baclofen solutions (0.05 mg/mL baclofen) were prepared at a Contract Manufacturing Organization (CMO) in accordance with instructions from the inventors. 1.96 mL of those baclofen solutions were placed in a 5 mL vial and steam sterilized ($F_0$ for 15 min. at 121.1° C.). Resultant 4-CPP levels and pH are presented in Table I below.

TABLE 1

| 4-CPP and pH following terminal sterilization | | |
|---|---|---|
| Run Number | 4-CPP Level (%) | pH |
| 1 | 1.92 | 7.0 |
| 2 | 1.96 | 6.9 |

These two runs resulted in a 4-CPP level higher than the Release Specifications. In addition, the pH of the resultant solutions was on the high side of the Release Specifications post terminal sterilization.

The following studies were conducted to identify changes that could be made in the heat sterilization methods with baclofen solutions of varying concentration and pH to obtain a terminally sterilized injectable baclofen solution meeting the pH and level of 4-CPP Release Specifications. Experiments to this effect are presented below in Example 2.

Example 2

Studies to Identify Process Changes to Address 4-CPP and pH Issues

Initially, a 0.05 mg/mL test batch was prepared by the CMO that resulted in elevated 4-CPP levels. As a result, the following studies were performed:

200 mL of 0.05 mg/mL baclofen was prepared using the following materials:
  Bacofen, USP API (batch 4010108)
  NaCl (Mallinckrodt Batch G31623)
  Water (Nanopure 18.2MΩ-cm)
  Nitrogen (Praxair 99.9999%, 6.0 research grade)
  Bottles (Qorpak Cat. No. 7968)

Nitrogen was bubbled into solution for the duration of compounding (mix time=30 minutes at room temperature). The solution was left on bench overnight to continue dissolution.

The 200 mL stock solution was then split into 6 aliquots (into Wheaton bottles 66021-453) and the pH of each aliquot was adjusted as shown below:
  A. 20 mL=No pH Adjustment
  B. 20 mL=pH 4
  C. 20 mL=pH 5
  D. 20 mL=pH 6
  F. 20 mL=pH 7
  F. 20 mL=pH 8

Each of the 6 aliquots above were subdivided further into 4 separate 5 mL aliquots (into Quorpak bottles 2504T):
  A. 3 aliquots to 50° C.
  B. 1 aliquot to refrigerator An overview of the method and design is presented in FIG. 1.

Figure 2:
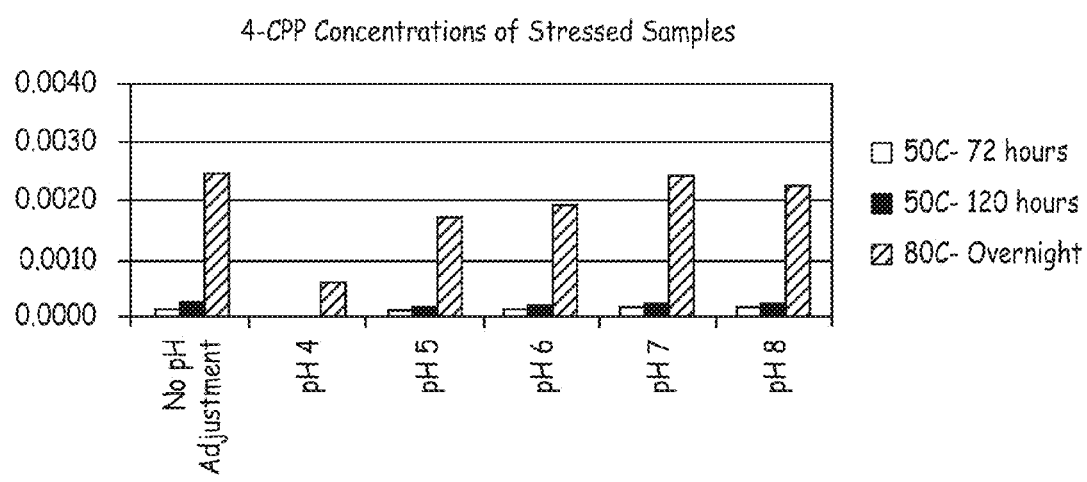
FIG. 2 is bar graph showing 4-CPP concentrations in various baclofen formulations subjected to a variety of conditions.

All samples were tested by HPLC after 3 days and essentially no increases in 4-CPP levels were detected. The solutions were split again so that half could be returned to the 50° C. incubator, while the other half could be placed into the 80° C. oven: 2 mL back into 50° C. incubator; 3 mL to 80° C. oven. Samples were retested after overnight incubations and the results are presented in FIG. 2.

The pH of the resulting solutions was also tested. The results are presented below in Table 2.

TABLE 2 pH results

|  | Initial | Post 3 days at 50 C. | Post 5 days at 50 C. | Post 5 days at 50 C. + Overnight | End of Study |
|---|---|---|---|---|---|
| No pH Adj. | 6.80 | 8.20 | 8.27 | 8.18 | 8.00 |
| pH4 | 3.98 | 7.65 | 7.56 | 7.96 | 6.95 |
| pH5 | 4.98 | 8.16 | 8.07 | 7.97 | 7.46 |
| pH6 | 5.95 | 7.86 | 8.09 | 8.23 | 7.78 |
| pH7 | 7.08 | 8.26 | 7.95 | 8.10 | 8.02 |
| pH8 | 8.00 | 8.36 | 8.04 | 7.97 | 8.06 |

The pH of each of the resulting solutions was out of range for the Release Specifications. It was thought that this might be due, in part, to the use of bottles that would not be used in manufacturing commercial products and were not the original vials were used in the experiments.

Similar studies were performed on solutions in their original vials. The results are presented below in Table 3.

TABLE 3 pH results in original vials

|  | Initial | Post Adjustment | End of Study |
|---|---|---|---|
| No pH Adj. | 6.80 | 6.80 | 6.75 |
| pH4 | 6.80 | 3.98 | 4.84 |
| pH5 | 6.50 | 4.98 | 6.46 |
| pH6 | 6.52 | 5.95 | 6.66 |
| pH7 | 6.54 | 7.08 | 6.77 |
| pH8 | 6.66 | 8.00 | 6.90 |

The results from these studies were determined to be inconclusive mainly because the solutions were initially aged at 50° C. without any noticeable increases in 4-CPP. When the solutions were later tested after exposure to 80° C., 4-CPP was observed.

Example 3

Further Evaluation of Sterilization of Process Changes Involving pH

Further studies were performed as outlined in Table 4 below.

TABLE 4

Phase I Studies

|  | 0.05 mg/mL (3 mL) | 0.5 mg/mL (20 mL) | 2.0 mg/mL (3 mL) | 2.0 mg/mL (20 mL) |
|---|---|---|---|---|
| General: Formulated stock solutions in Qorpak bottles Bubbled nitrogen at room temp Allowed solutions to sit overnight at room temp Split solutions for pH per studies A, B, C | X | X | Same stock solutions split later into vials | |
| Study A: Titrated to pH 6 Transferred vials at production volume Nitrogen overlay Sterilized 10, 20, 30 min | X | N/A | N/A | N/A |
| Study B: Titrated to pH 6 Transferred vials at production volume Nitrogen overlay Sterilized 10, 20, 30 min | X | N/A | N/A | N/A |
| Study C: No pH adjustment Transferred vials at production volume Nitrogen overlay Sterilized 10, 20, 30 min Measured pH, Assayed, Related Substances | N/A | X | Same stock solutions split later into vials | |
| Study D: Fill Volume Study Using formulations from Studies A and B, filled a set of 5 mL vials with 1 mL solution, and another set with 4 mL solution Process as in Study A | X | N/A | N/A | N/A |
| Study E: Vial leachable profile Ran water controls same as Study A Leachable profile | X | X | X | X |
| Study F: Stopper effect/Stability Formulated enough Study A and Study B solutions (20 min autoclave) to compare inverted vs. upright over time Storage: accelerated 37° C., 5° C. upright control Duration: 3 months with pulls are T = 0, D7, D14, D28, 3 Month Measure assay, 4-CPP | X | X | N/A | N/A |
| Study G: Chloride concentration effect Formulation 0.05 mg/mL with: 0.0% NaCl 0.4% NaCl 0.9% NaCl Adjusted to pH 6. Ran same as Study A | X | N/A | N/A | N/A |
| Study H: 4-CPP effect on 4-CPP Took aliquots of Study A formulation, spiked with 4-CPP: | X | N/A | N/A | N/A |

TABLE 4-continued

Phase I Studies

| | 0.05 mg/mL (3 mL) | 0.5 mg/mL (20 mL) | 2.0 mg/mL (3 mL) | 2.0 mg/mL (20 mL) |
|---|---|---|---|---|
| 0.1% (2 mg/mL only) | | | | |
| 0.5% (2 mg/mL only) | | | | |
| 1.0% (2 mg/mL only) | | | | |

For Phase 1 studies A, B, C, D, F, and H, the solutions were formulated at room temperature (≈22° C.) with N2 bubbling during mixing. Baclofen, USP was evaluated from two API suppliers. The solutions were formulated using Nanopure water and NaCl, rather than using pre-made USP 0.9% Saline. Stock volumes were prepared as follows: (i) 0.05 mg/mL=150 mL; (ii) 0.5 mg/mL=750 mL and (iii) 2.0 mg/mL=350 mL. The mix times used were: (i) 0.05 mg/mL≈20-30 minutes; (ii) 0.5 mg/mL≈30 minutes; and (iii) 2.0 mg/mL>30 minutes stirring followed by brief sonication. All formulations were left on the lab bench overnight (≈22° C.) after mixing so that dissolution could continue. The 0.05 mg/mL stock solutions were split into two bottles and pH adjusted per study requirements: Study A adjusted to pH 6.0; Study B adjusted to pH 4.0. The 0.5 mg/mL and 2.0 mg/mL formulations were adjusted to pH 6.0.

Figure 3:
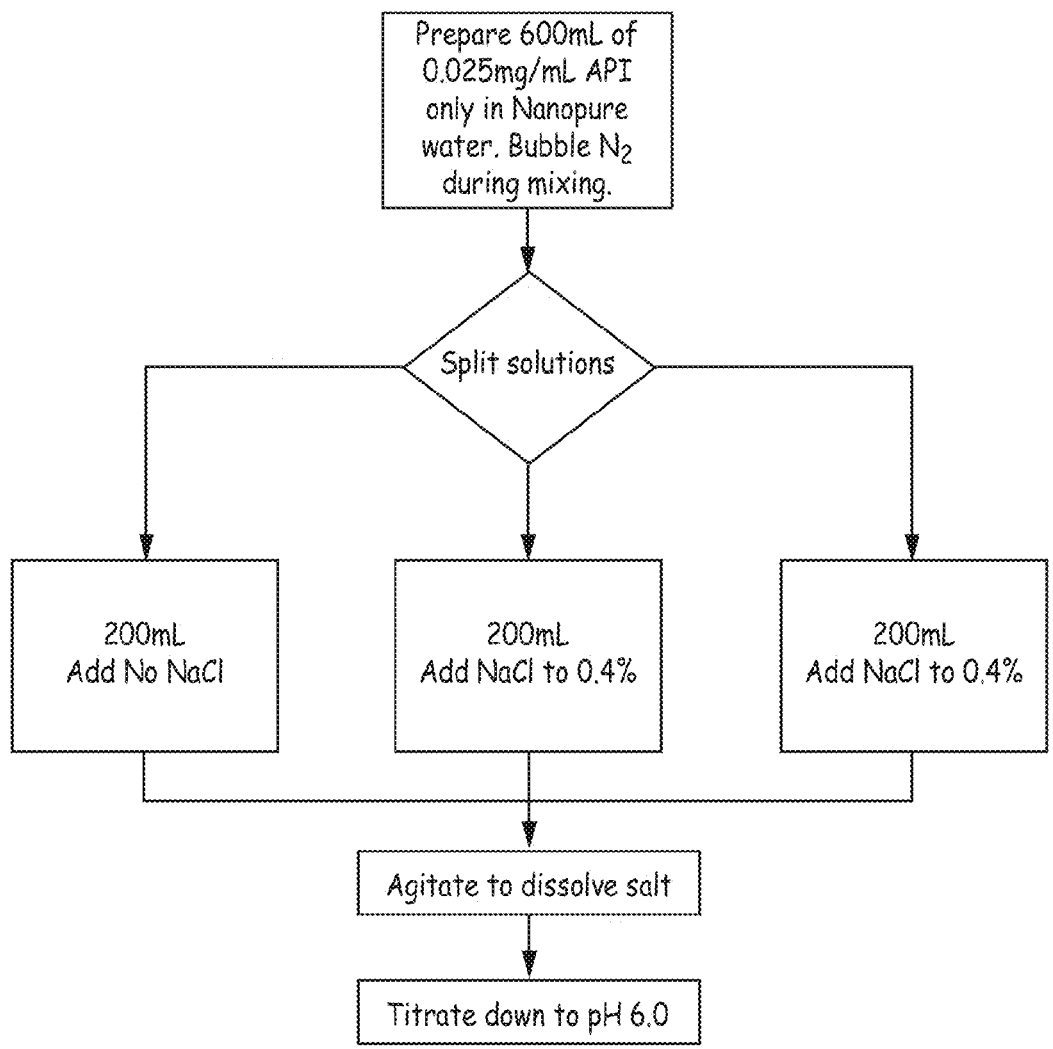
FIGS. 3-5 are flow diagrams providing overviews of the preparation of baclofen formulations that were generated and tested in accordance with an Example presented herein.

For Study G, the solutions were formulated using Baclofen, USP from two different suppliers at room temperature (≈22° C.) with $N_2$ bubbling during mixing. An overview of the preparation is provided in FIG. 3.

Figure 4:
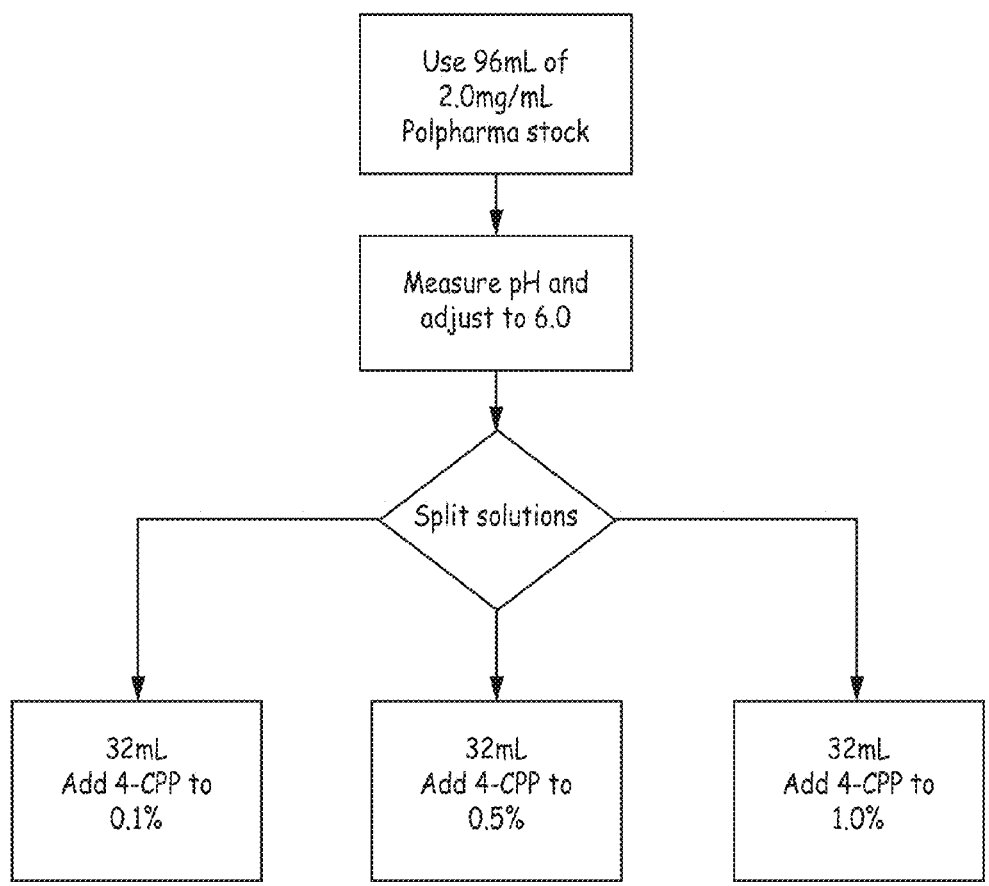

For Study H, the solutions were prepared from the 2.0 mg/mL baclofen stock solution used in Studies A, B, C, D, and F as outlined in FIG. 4.

Figure 5:
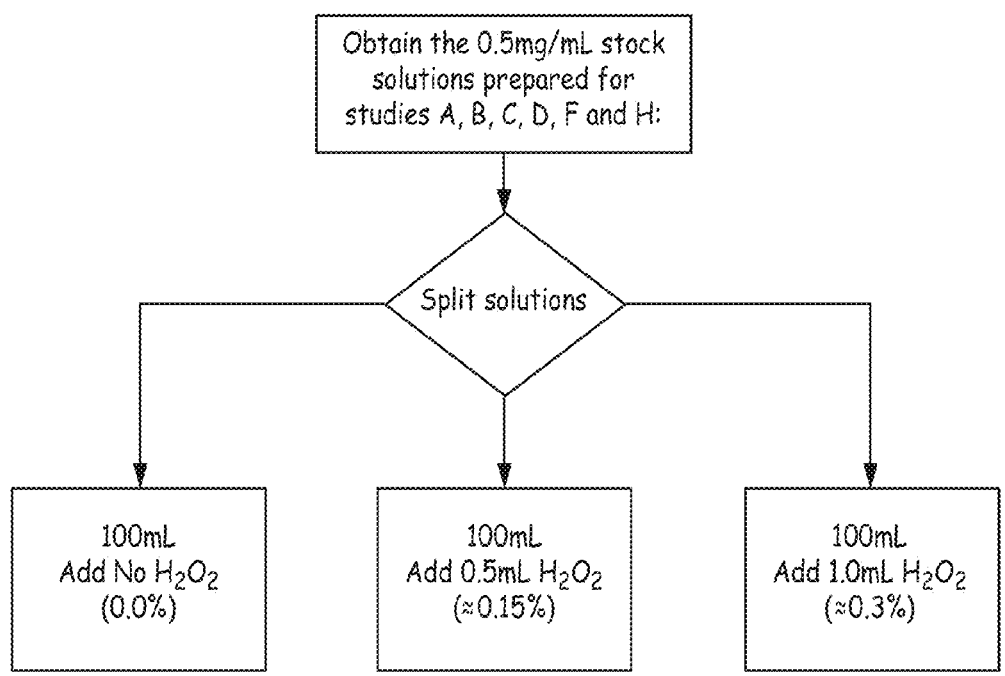

Additional samples were prepared and spiked with hydrogen peroxide to study the effects of extreme oxidation on baclofen. Samples were prepared as presented in FIG. 5. All formulations were filled into vials supplied from the CMO and a nitrogen blanked was applied. All formulations were terminally sterilized at 121° C. for 20 min. using moist heat.

These initial studies (data not shown) indicate that the formulation factors having the largest effect on the formation of 4-CPP upon terminal sterilization are (i) headspace; (ii) presence of oxygen (related to headspace); (iii) NaCl concentration; and (iv) pH.

Additional studies (not shown) were performed, which indicated that pH may be the primary variable associated with 4-CPP levels.

Example 4

Determination of pH Stability

Prior experiments have shown that adjusting the pH of baclofen formulations after sufficient mixing, but prior to terminal sterilization, results in favorable 4-CPP levels.

The purpose of this experiment was to determine the 4-CPP levels formed for a 0.5 mg/mL baclofen formulation at pH values of 3, 4, 5, 6, 7, 8, 9, and 10.

Figure 6:
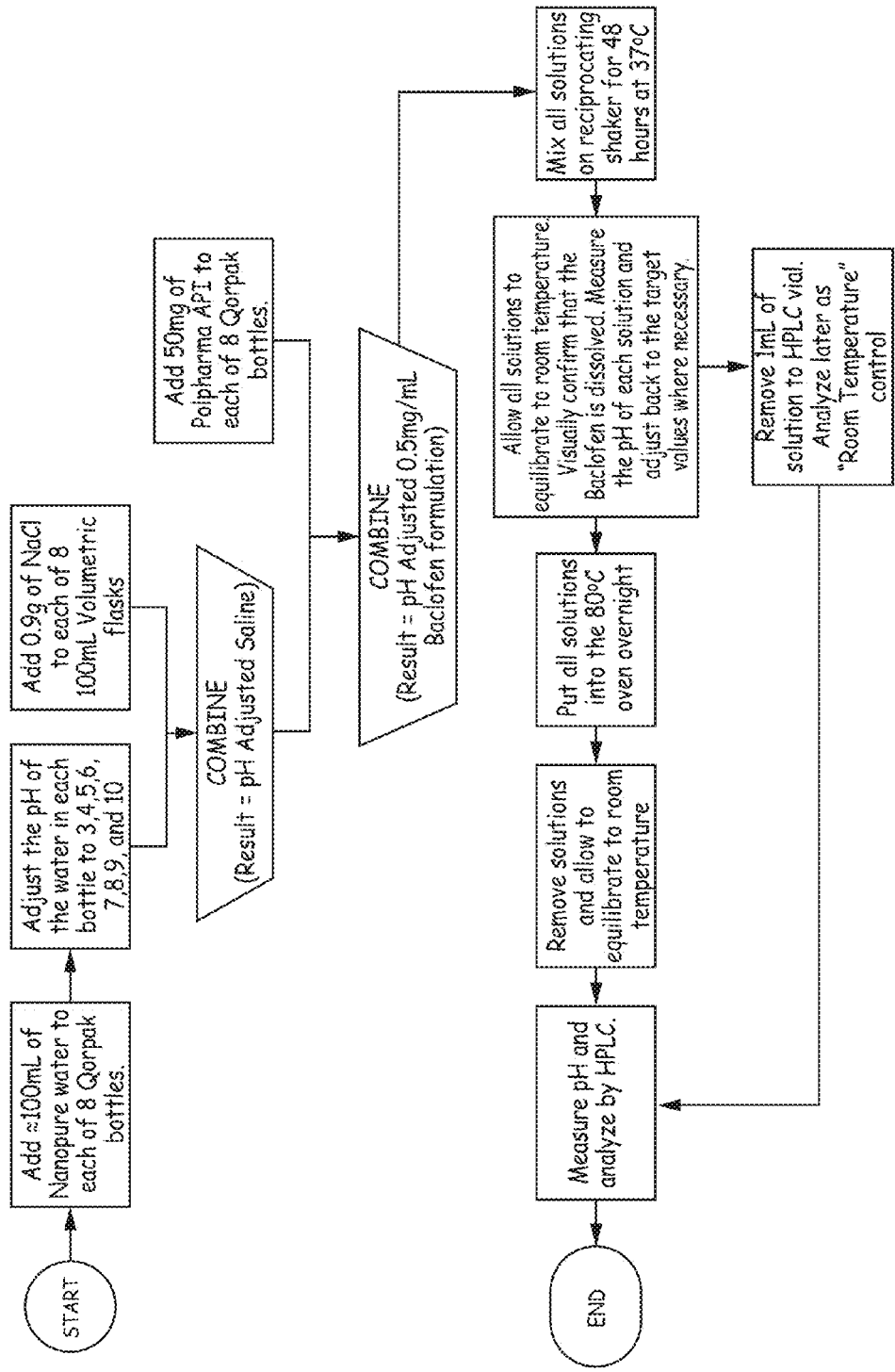
FIG. 6 is a flow diagram illustrating a study design and methods employed in an Example presented herein.
Figure 7:
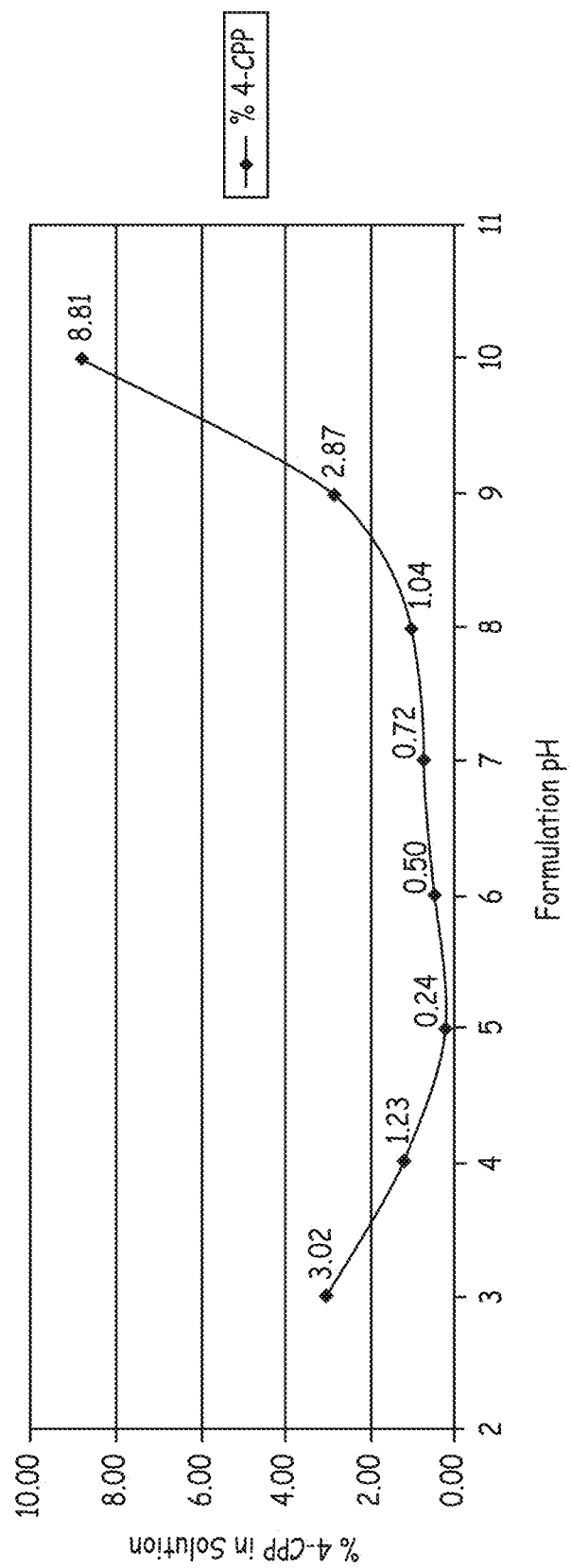
FIG. 7 is a graph of 4-CPP concentration in various baclofen formulations tested as described in an Example presented herein.

The study design and methods are presented in FIG. 6. Results are presented in FIG. 7, where samples were subjected to 80° C. for 24 hours.

Figure 8:
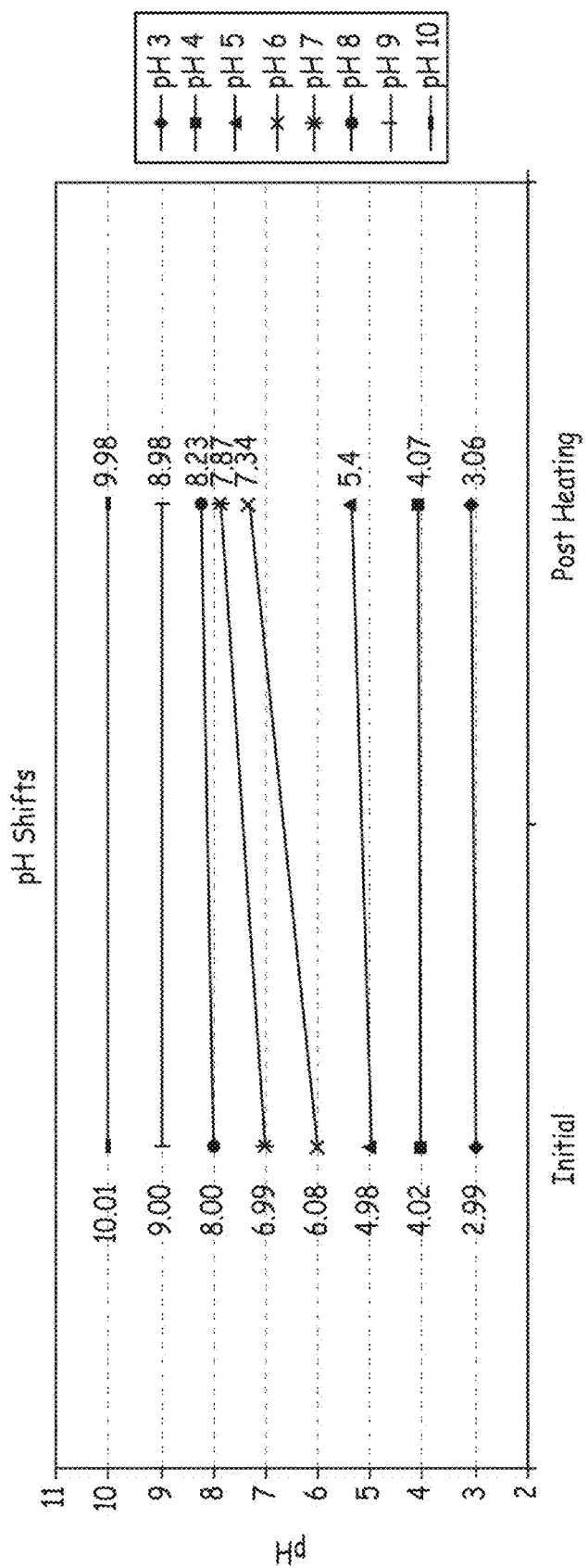
FIG. 8 is a graph showing pH shifting of various baclofen formulations following heat treatment as described in an Example presented herein.

As described in FIG. 6, the pH was adjusted to values of 3, 4, 5, 6, 7, 8, 9, and 10 after mixing for 48 hours at 37° C., prior to heating to 80° C. The pH was then measured again at the end of the experiment to determine if the pH had shifted during overnight heating at 80° C. The results are presented in FIG. 8.

Several conclusions may be reached from this study. While a 1 hour mix time works well for the 0.05 mg/mL formulation, as demonstrated in previous experiments, the higher concentration of 0.5 mg/mL required a longer mix time. To minimize 4-CPP formation, the pH of the solution should be adjusted, after sufficient mixing, but prior to applying heat (by autoclave in the production environment, or by oven in the lab environment). The curve generated by this experiment indicates that the lowest levels of 4-CPP are observed in the formulations adjusted to pH 5-6. pH does appear to drift for some formulations, but not for others, as heat is applied.

Example 5

Additional pH Testing

This study was designed to expand upon the previous experiment which showed that a 0.5 g/mL baclofen formulation produced the least 4-CPP when the pH was adjusted to ≈5.0 prior to heat exposure in an 80° C. lab oven. In this experiment, the 80° C. oven experiment was repeated, but with the addition of pull points at T=4 days and T=8 days. This study included: (i) additional pH points to the curve to more clearly show the suitable formulation pH prior to terminal sterilization; (ii) use of the 0.05 mg/mL formulation; (iii) use of the autoclave to mimic terminal sterilization; and (iv) use of CMO vials, stoppers, and seals.

Figure 9:
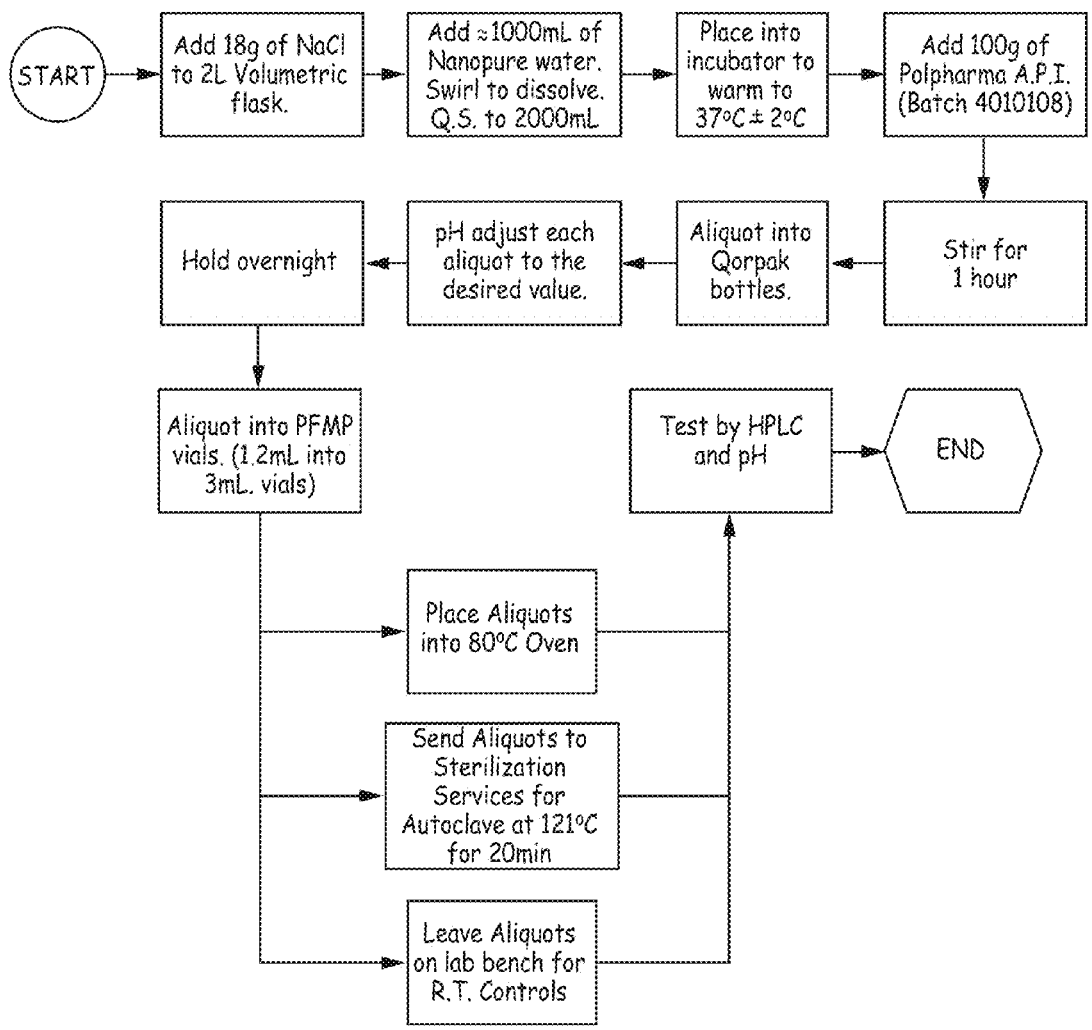
FIG. 9 is a flow diagram illustrating an experimental design employed in an Example presented herein.

The experimental design is presented in FIG. 9.

Figure 10:
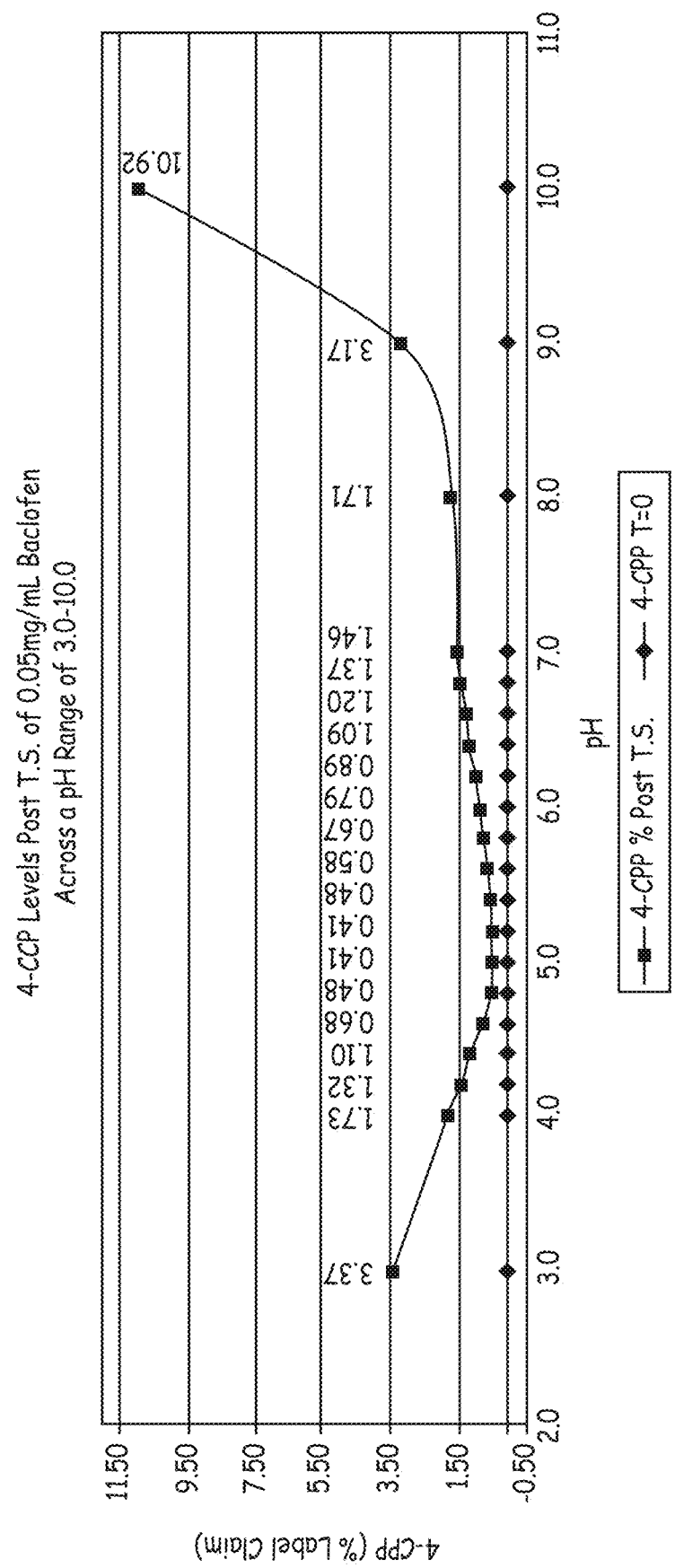
FIG. 10 is a graph of 4-CPP concentration in various baclofen formulations tested as described in an Example presented herein.

The results are presented in FIG. 10, where each point on the graph is an average of three separate replicate vials.

Figure 11:
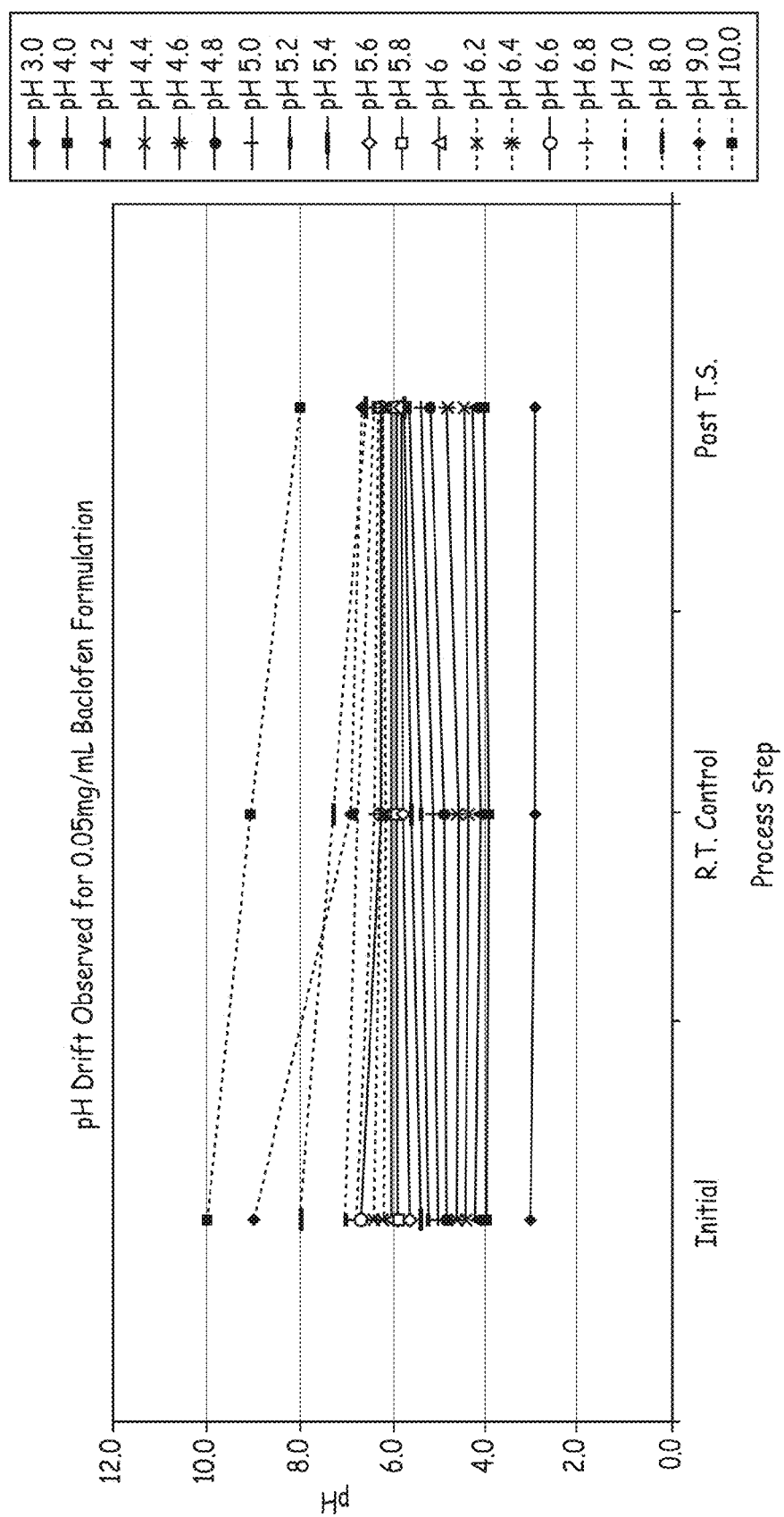
FIGS. 11-12 are graphs showing pH shifting of various baclofen formulations following heat treatment as described in an Example presented herein.
Figure 12:
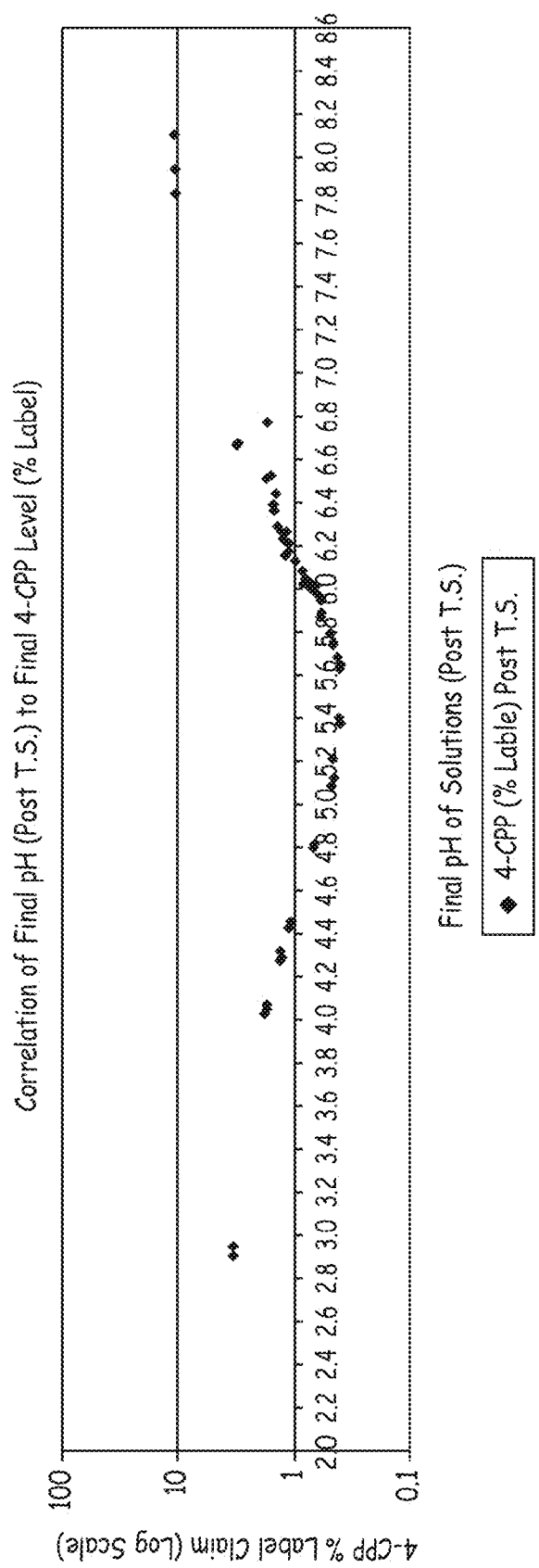

The results of pH shift are presented in FIG. 11. In FIG. 12, the data are plotted as Final Solution pH vs. 4-CPP (% label). The significance of pH "drift" can be seen in FIG. 12. For example, the formulation that is initially adjusted to pH 5.2, drifted up to ≈pH 5.7 post terminal sterilization.

Figure 13:
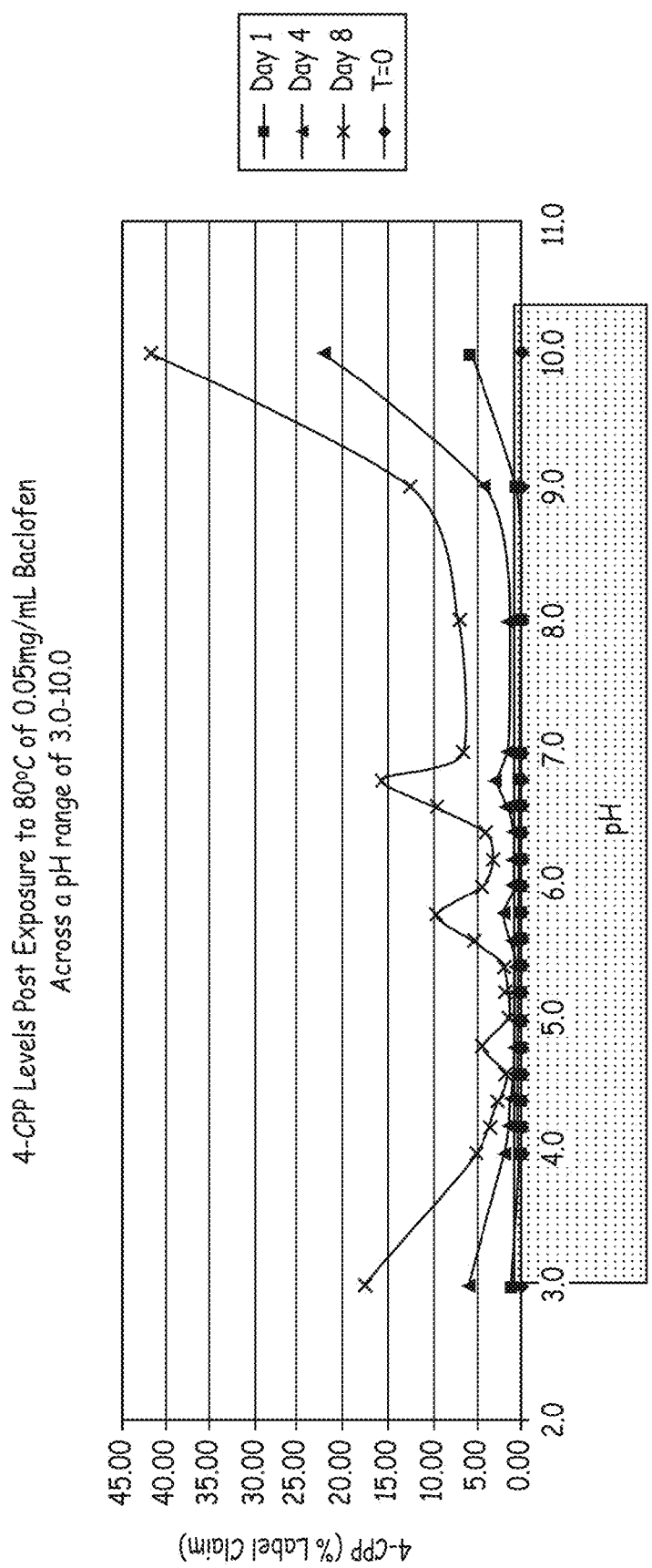
FIGS. 13-14 are graphs of 4-CPP concentration in various baclofen formulations tested as described in an Example presented herein.
Figure 14:
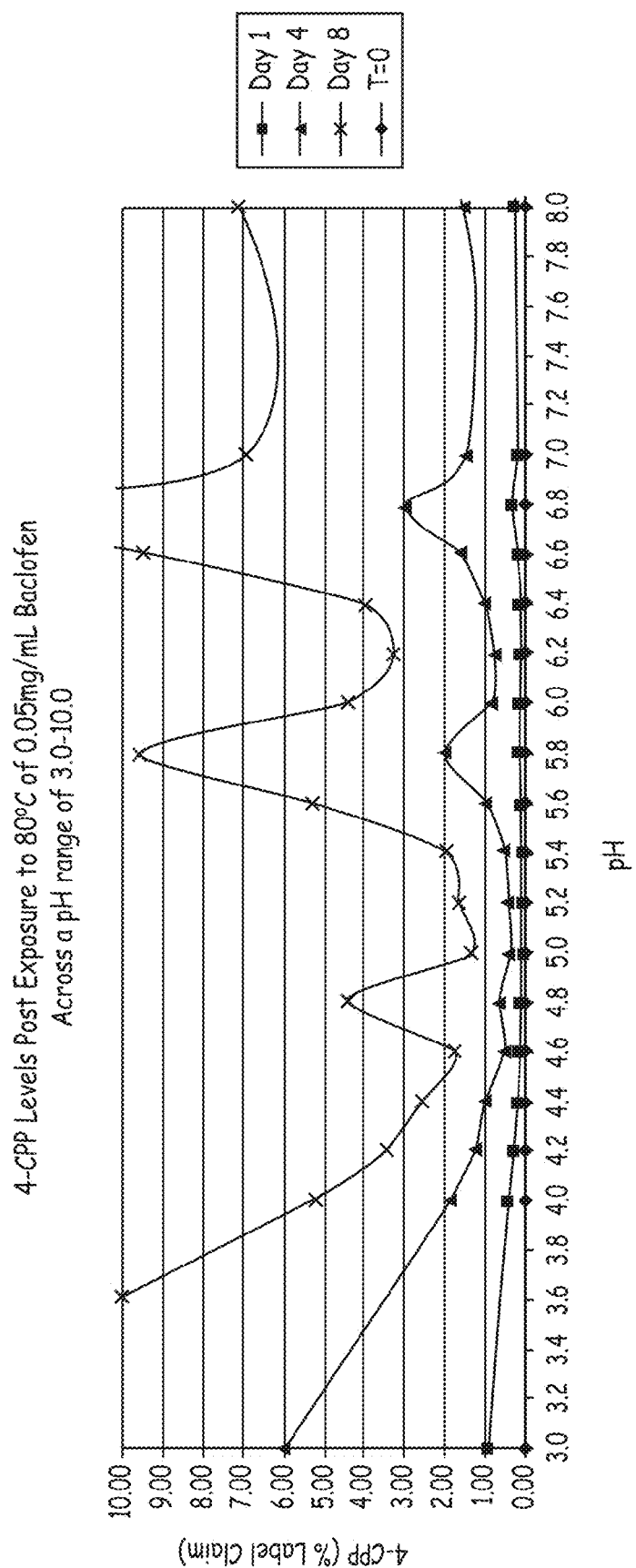
Figure 15:
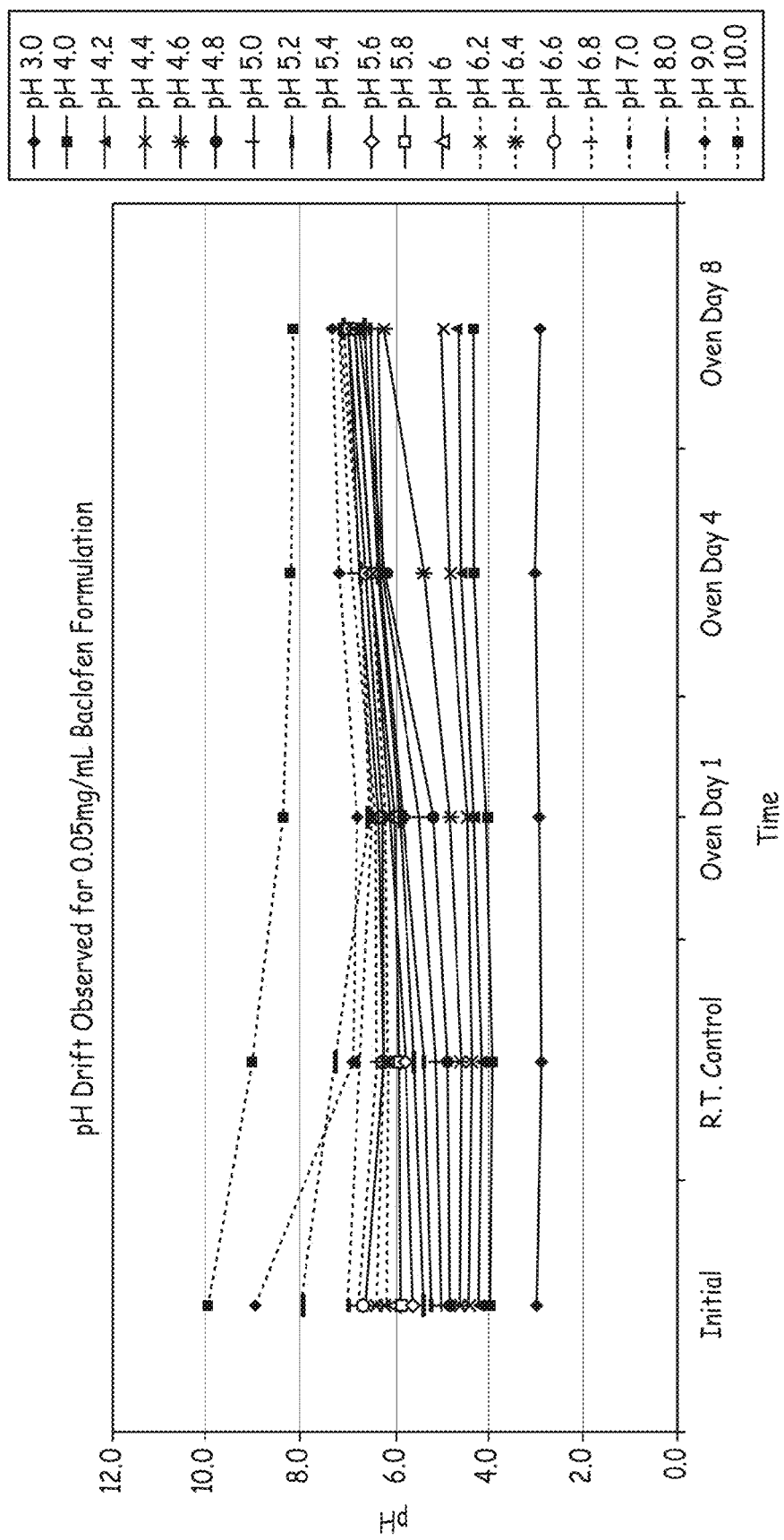
FIG. 15 is a graph showing pH shifting of various baclofen formulations following heat treatment as described in an Example presented herein.
Figure 16:
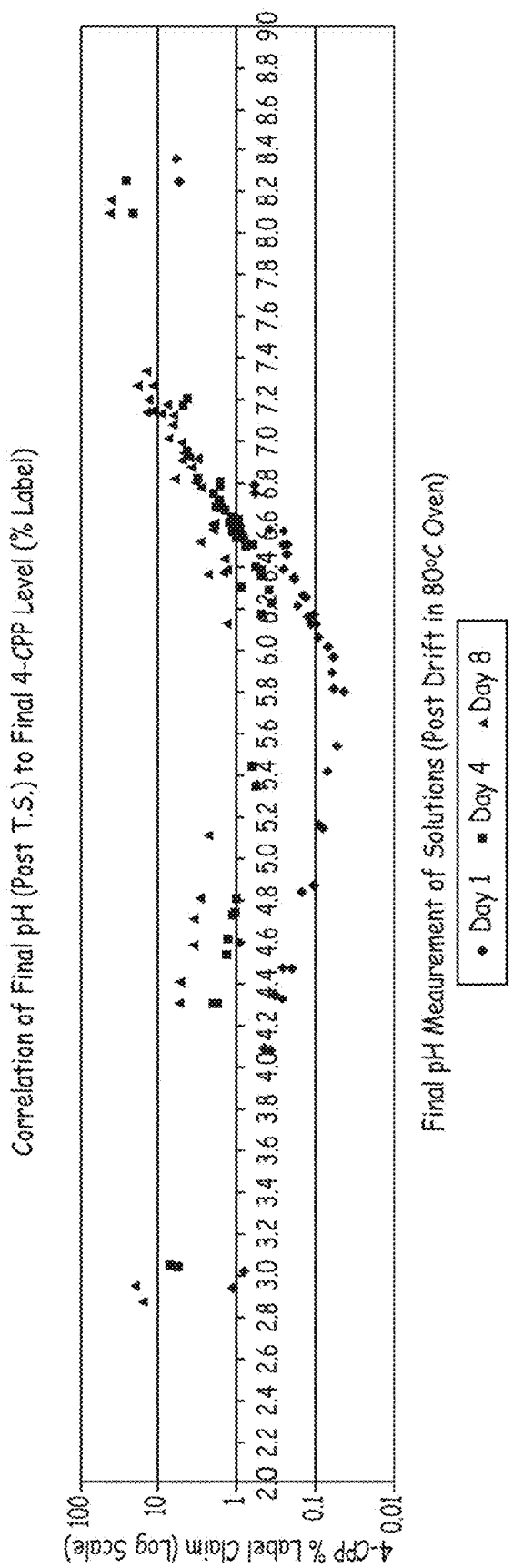
FIG. 16 is a graph showing the correlation between final pH and concentrations of 4-CPP in various baclofen formulations tested as described in an Example presented herein.

Additional 4-CPP results are presented in FIGS. 13-14, where FIG. 14 is a magnified view of a portion of FIG. 13. Additional pH shift results are presented in FIG. 15. Additional Final Solution pH vs. 4-CPP are presented in FIG. 16.

As seen in previous experiments, there is significant pH "drift". If the starting formulation is at pH 5.2, it will likely drift up to ≈pH 5.8 after one day of exposure to 80° C. in the lab oven.

Based on these results, it is concluded that adjusting the pH to ≈5.2 prior to terminal sterilization may be desirable. A "window" for pH adjustment that may be suitable is 5.0-5.4.

Additional studies were performed on 0.5 mg/mL baclofen formulations (data not shown). Similar results were observed. Specifically, pH adjustment to 5.4 before terminal sterilization produced the lowest observed 4-CPP levels.

The following observations and conclusions were also noted: (i) nitrogen bubbling tended to increase the pH of the solution, so the pH adjustment step should consider additional HCl to compensate; and (ii) pH drift was more pronounced for the 0.05 mg/mL formulation than for the 0.5 mg/mL formulation.

Based on the results of testing, it was determined that adjusting the pH to 5.2 for the 0.05 mg/mL formulation resulted in the lowest observed 4-CPP levels. However, adjustment to pH 5.3 may be desired to ensure that the final pH falls within the desired specifications (pH 5.0-7.0); e.g., around pH 6.0.

For the 0.5 mg/mL formulation, adjustment to pH 5.4 resulted in the lowest 4-CPP levels. However, adjustment to pH 5.5-5.8 may be desired to ensure that the final pH falls within the desired specifications (pH 5.0-7.0); e.g., around pH 6.0.

Example 6

Studies at the CMO with Process and Compounding Parameters

Additional work was conducted with various volumes and concentrations of baclofen solutions compounded and subjected to terminal sterilization using the parameters described presented below in Table 5.

TABLE 5

Compounding of Baclofen Solutions for Testing

| Product Configuration | Compounding Temperature | Pre pH Adjustment Stir Time | End of Compounding pH | Dissolved Oxygen Post pH | Headspace Oxygen During Filling |
|---|---|---|---|---|---|
| 1 mL (0.05 mg/mL) | 45° C. to 50° C. | 10 min | 6.0 ± 0.1 | <1 ppm | <10% |
| 5 mL (2.0 mg/mL) | 45° C. to 50° C. | 10 min | 6.0 ± 0.1 | <1 ppm | <10% |
| 20 mL (0.5 mg/mL) | 45° C. to 50° C. | 10 min | 6.0 ± 0.1 | <1 ppm | <10% |

Following terminal sterilization, the concentration of baclofen, pH and 4-CPP (% total initial baclofen) were determined. The results are presented below in Table 6.

TABLE 6

Results of Terminal Sterilization

| Product Configuration | Baclofen (mg/mL) | pH | 4-CPP |
|---|---|---|---|
| 1 mL (0.05 mg/mL) | 0.0485 | 7.1 | 2.2% |
| 5 mL (2.0 mg/mL) | 2.0 | 6.2 | 0.7% |
| 20 mL (0.5 mg/mL) | 0.499 | 6.4 | 1.1% |

From these results, the observation that pH tends to increase following terminal sterilization was confirmed. This is likely due to the fact that these are not buffered solutions. In addition, the percent of 4-CPP tends to be higher with lower baclofen concentrations.

Production of Baclofen solutions meeting the Release Specification was achieved using the process and compounding parameters described below in Table 7.

TABLE 7

Baclofen Parameters

| Product Configuration | Compounding Temperature | Pre pH Adjustment Stir Time | End of Compounding pH | Dissolved Oxygen Post pH | Headspace Oxygen During Filling |
|---|---|---|---|---|---|
| 1 mL (0.05 mg/mL) | 32° C. to 37° C. | 90 ± 10 min | 5.3 ± 0.1 | <1 ppm | <10% |
| 5 mL (2.0 mg/mL) | 32° C. to 37° C. | 90 ± 10 min | 6.0 ± 0.1 | <1 ppm | <6% |
| 20 mL (0.5 mg/mL) | 32° C. to 37° C. | 90 ± 10 min | 5.8 ± 0.1 | <1 ppm | <10% |

Following terminal sterilization of the solutions in Table 7, the concentration of baclofen, pH and 4-CPP (% total initial baclofen) were determined. The results are presented below in Table 8.

TABLE 8

Results of Terminal Sterilization

| Product Configuration | Baclofen (mg/mL) | pH | 4-CPP |
|---|---|---|---|
| 1 mL (0.05 mg/mL) | 0.0499 | 5.9 | 0.4% |
| 5 mL (2.0 mg/mL) | 1.96 | 6.1 | 0.6% |
| 20 mL (0.5 mg/mL) | 0.494 | 5.9 | 0.7% |

Conclusions

The formulation development studies and full scale batch manufacturing (Table 7 parameters) described above demonstrated that the pH of the formulation prior to terminal sterilization is the most controlling process parameter to determining post sterilization pH and 4-CPP amounts. The studies also demonstrated that the formulation pH can be affected by long process hold times, as well as the presence of dissolved $N_2$ in the formulation (both of which can cause the pH to drift upward).

Successful batch manufacture of the 0.5 mg/mL formulation occurred when the pH was adjusted to 5.8±0.1 prior to terminal sterilization, resulting in a final product with 4-CPP levels of 0.7%.

Successful batch manufacture of the 0.05 mg/mL formulation occurred when the pH was adjusted to 5.3±0.1 prior to terminal sterilization, resulting in a final product with 4-CPP levels of 0.4%.

Based on the results of these studies, it is believed that a pH adjustment to 5.8±0.1 will result in a 4-CPP level for the 2.0 mg/mL formulation that would be lower than the level observed with a pH of 6.0±0.1.

While compounding temperature and mix time are not as controlling as compounding pH with regard to ultimate pH or 4-CPP level, they should be carefully controlled to ensure complete dissolution of the baclofen.

Based on these studies, there was no clear indication that oxygen had a significant role in determining pH or 4-CPP levels following terminal sterilization.

Example 8

Solubility of Baclofen

A variety of tests were performed to determine whether concentrations of baclofen greater than 2 mg/mL could be achieved, while maintaining stability (e.g., low 4-CPP).

The salts presented in Table 9 below were tested for their effect on the solubility and stability of baclofen.

TABLE 9

Formulation Experimental Design

| Anion | Acid to Adjust | Cation | Base to Adjust |
| --- | --- | --- | --- |
| Chloride | HCl | $Na^+$ | NaOH |
| Phosphate, monobasic | Phosphoric Acid | $Mg^{2+}$ | $Mg(OH)_2$ |
| Sulfate | Sulfuric Acid | | |
| Nitrate | Nitric Acid | | |
| Acetate | Acetic Acid | | |
| Sucrose | | | |

From these tests, it was found that a high concentration (greater than 4 mg/mL) of baclofen could be achieved with similar stability to Lioresal® Intrathecal. Phosphate and sulfate were determined to be the best salts.

Figure 17:
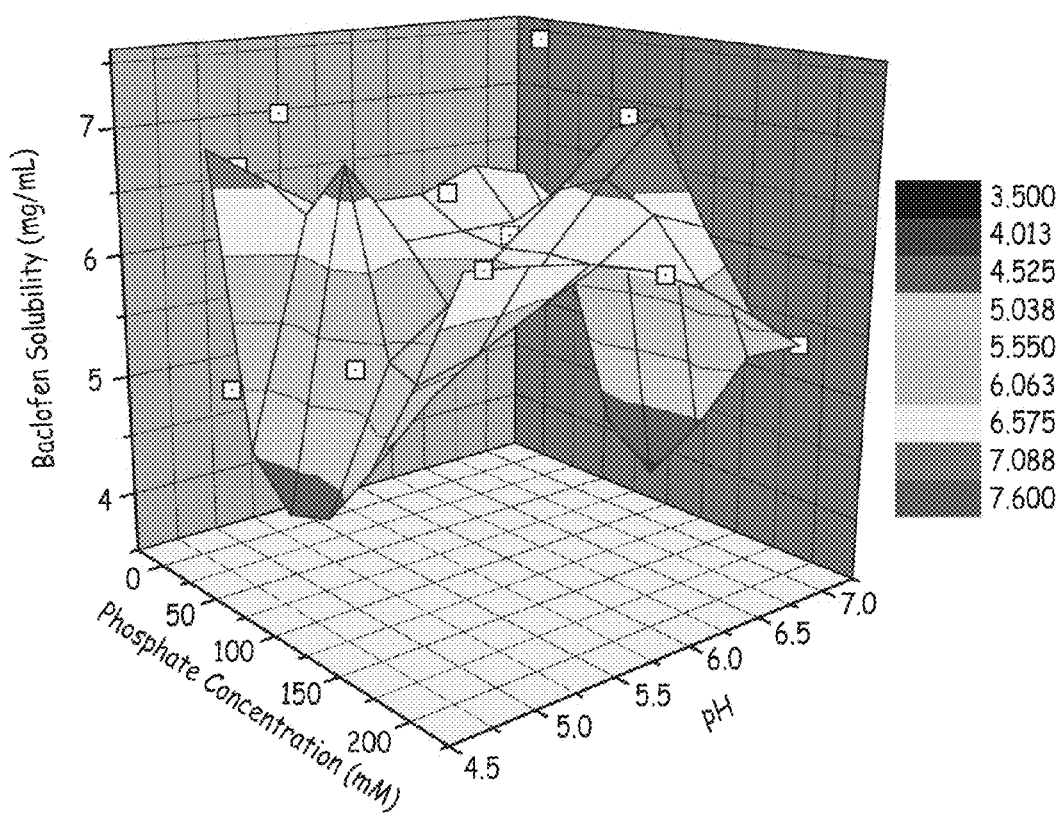
FIGS. 17-18 are three dimensional plots of baclofen solubility, phosphate concentration and pH of various baclofen formulations tested as described in an Example presented herein.
Figure 18:
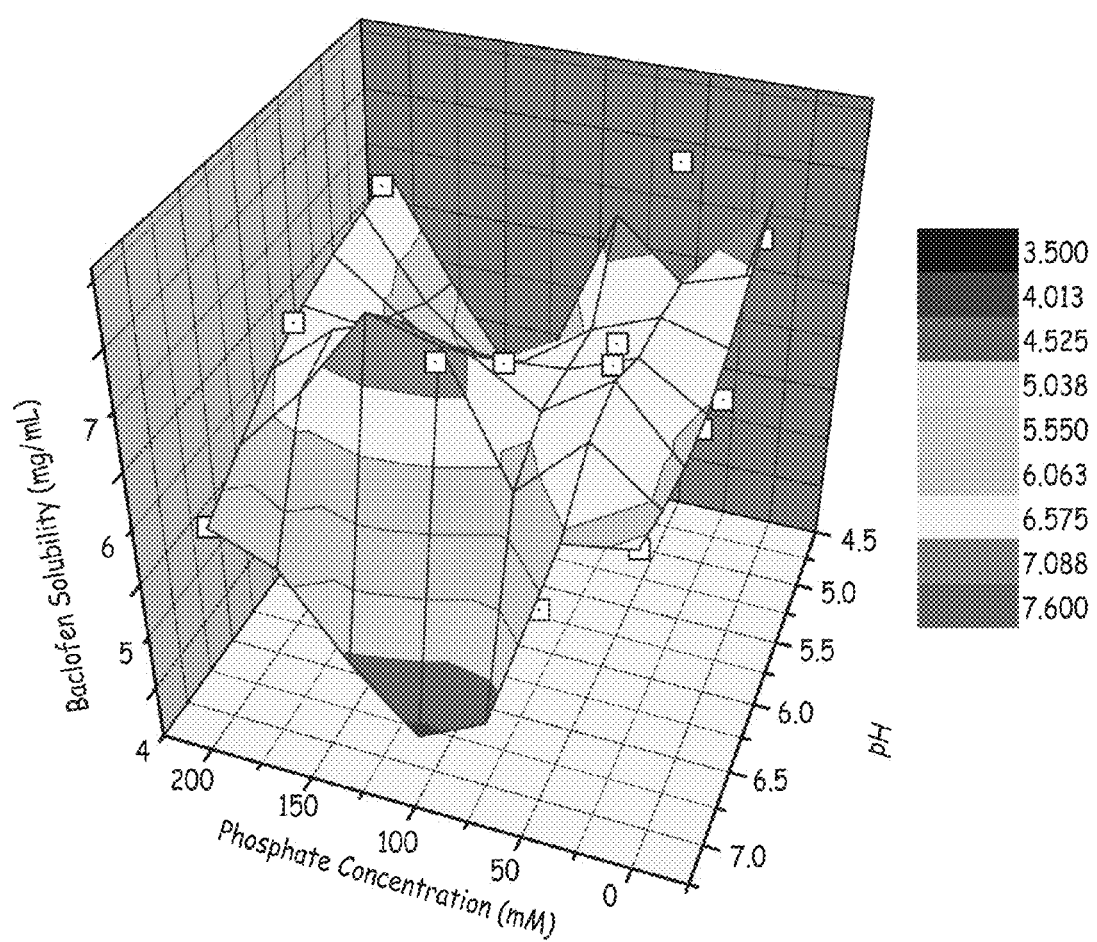
Figure 19:
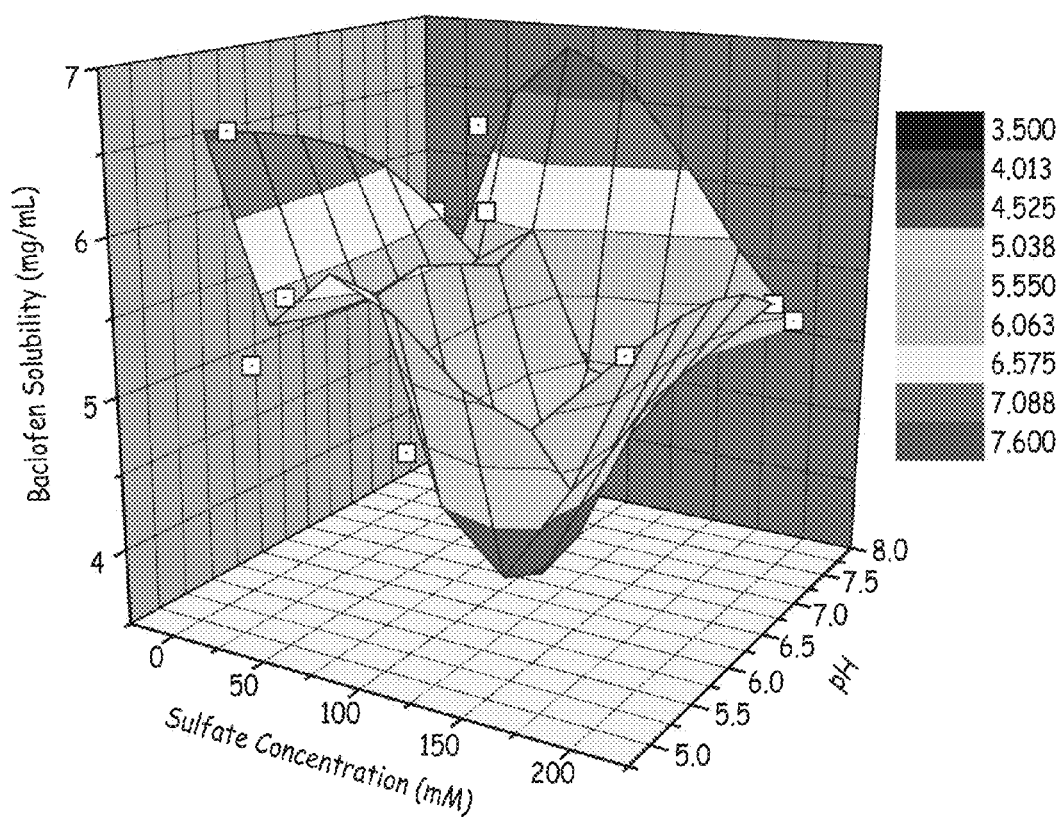
FIG. 19 is a three dimensional plot of baclofen solubility, sulfate concentration and pH of various baclofen formulations tested as described in an Example presented herein.

Results for solubility of baclofen in different concentrations of phosphate at different pH levels are shown in FIGS. 17-18, and results for solubility of baclofen in different concentrations of sulfate at different pH levels are shown in FIG. 19. The results presented are at 4 weeks.

Based on these studies, it was determined that low concentration phosphate or sulfate (e.g., less than or equal to 25 mM) with NaCl to maintain ionic strength at 0.154 M (NaCl eq.), pH 6 was a good solution for high concentration baclofen.

Example 9

Stability of Baclofen in Sulfate or Phosphate Solutions

L-baclofen was formulated and sterilized at concentrations of 0.05, 0.5, 2 and 4 mg/mL in phosphate and sulfate buffers (5, 10, and 25 nM), with NaCl to maintain ionic strength (1.54 M), pH 6. Lioresal® Intrathecal was used as a control.

The formulations were stored at 37° C., ambient temperature, and 4° C. over 9 weeks. pH, drug concentration, and 4-CPP were measured. Physical properties, such as particulate, precipitation, color and the like were observed.

Figure 20:
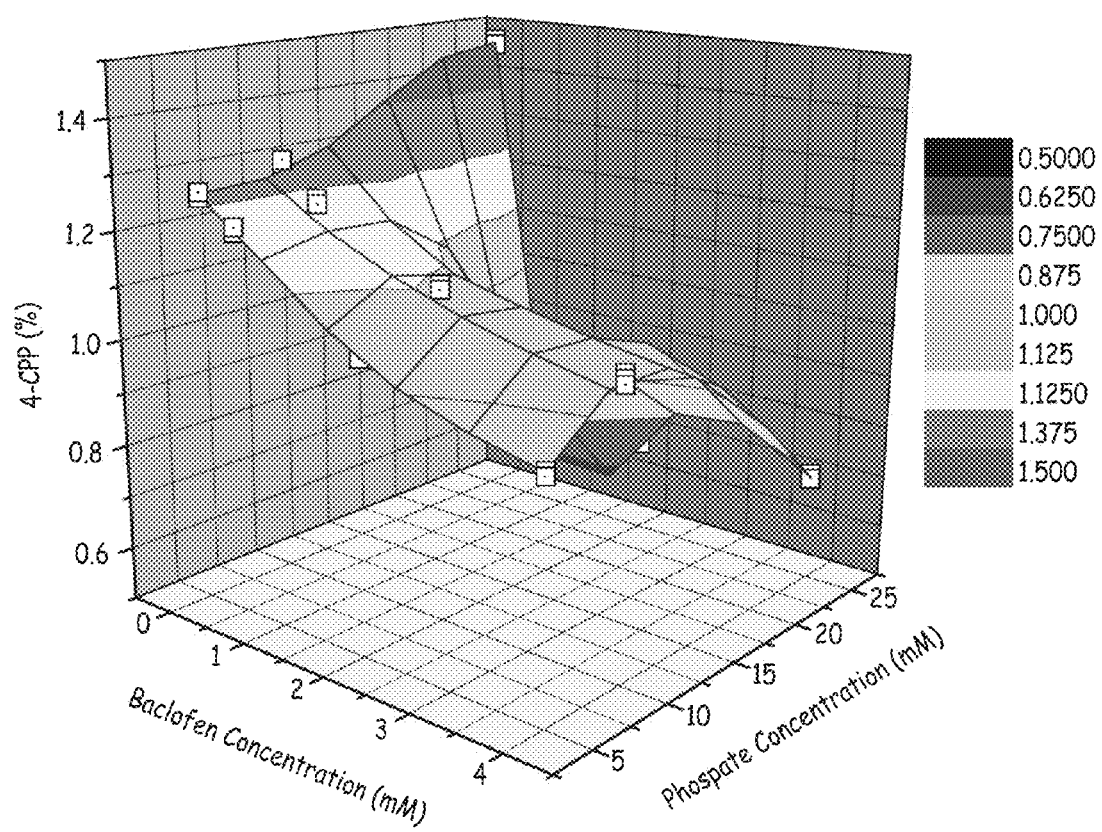
FIGS. 20-21 are three dimensional plots of 4-CPP concentration, baclofen concentration, and phosphate concentration of various baclofen formulations tested as described in an Example presented herein.
Figure 21:
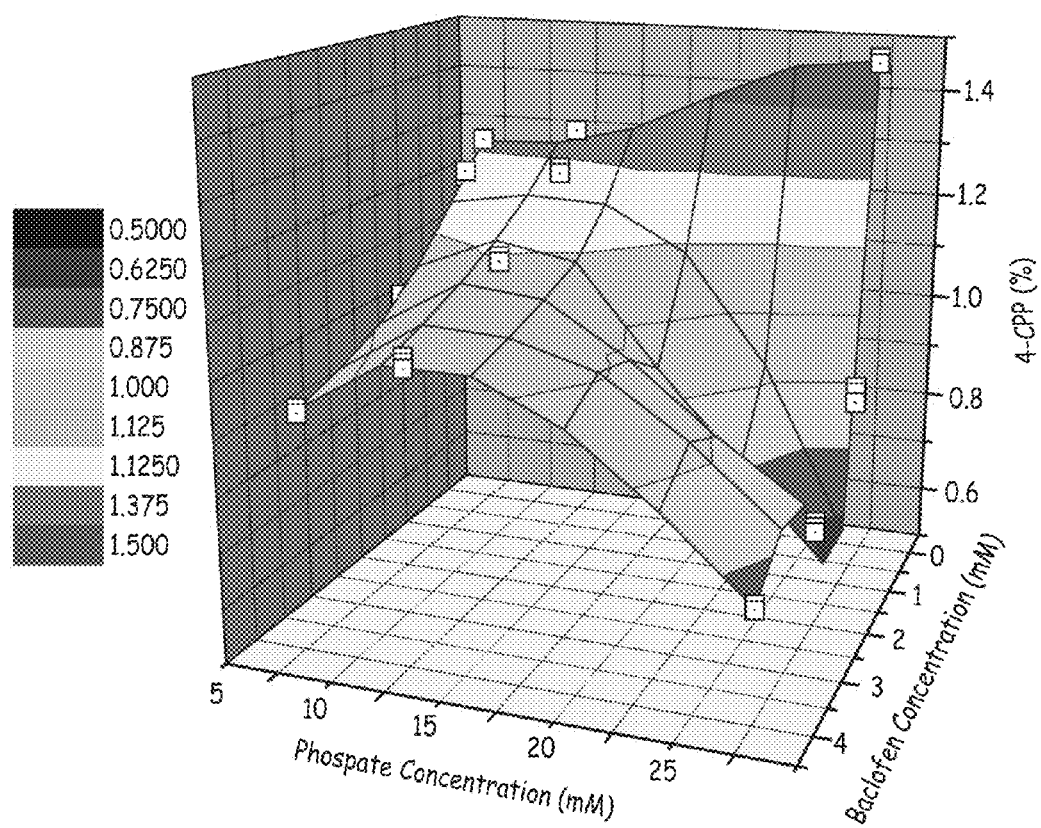
Figure 22:
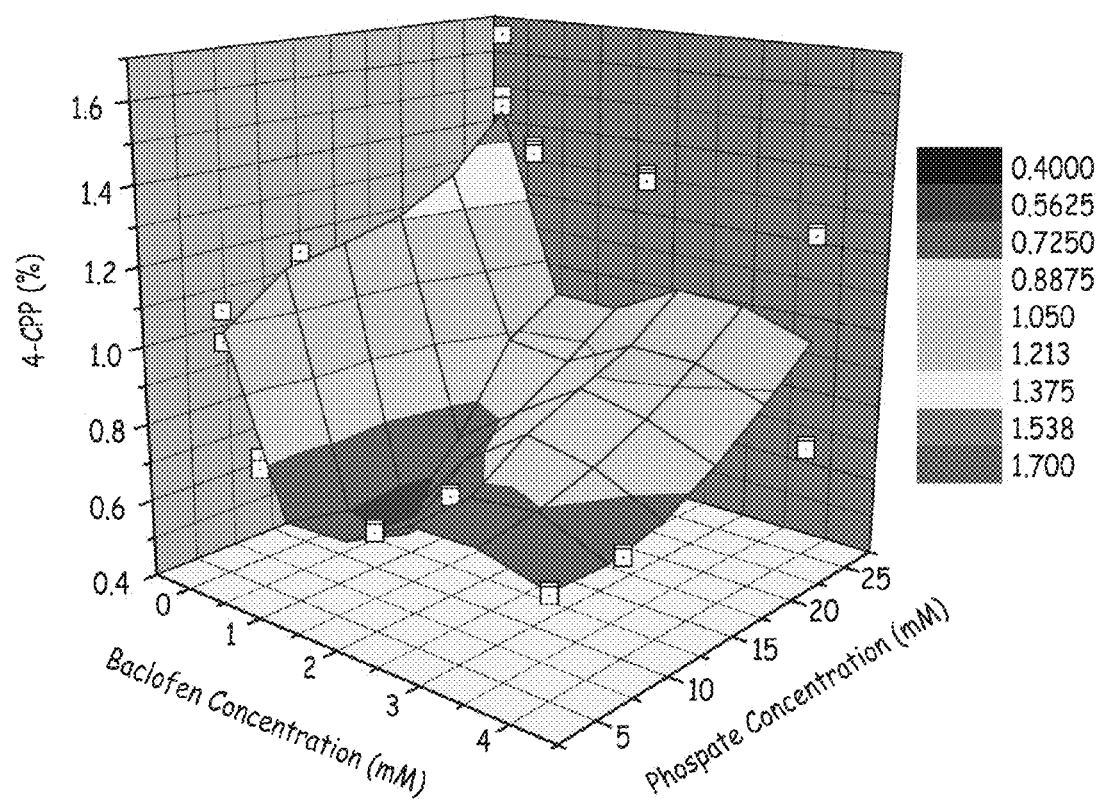
FIG. 22 is a three dimensional plot of 4-CPP concentration, baclofen concentration, and sulfate concentration of various baclofen formulations tested as described in an Example presented herein.
Figure 23:
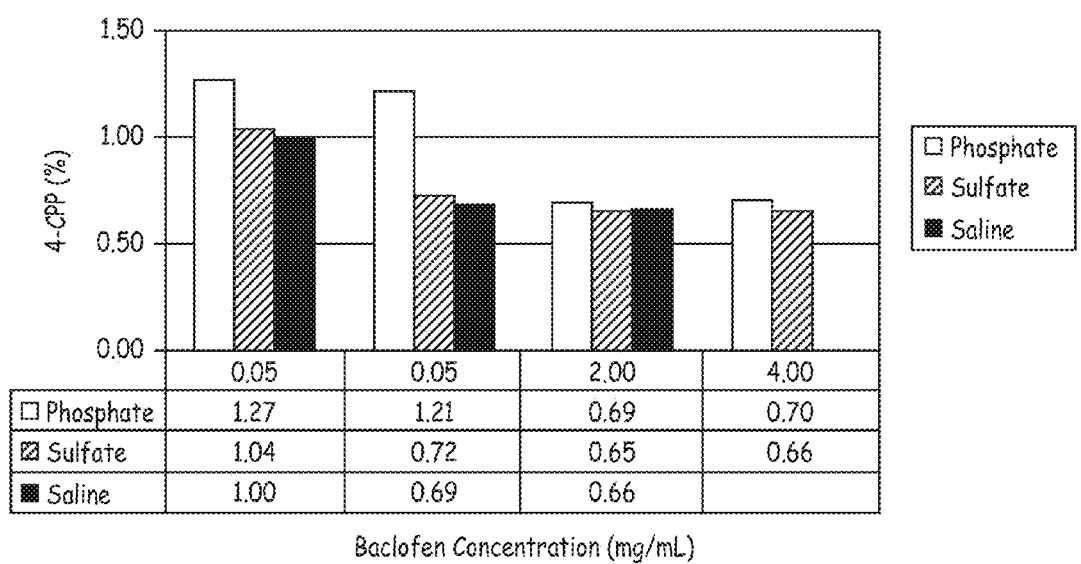
FIGS. 23-24 are bar graphs showing 4-CCP concentration of various baclofen formulations tested as described in an Example presented herein.

Results of the levels of 4-CCP observed at various phosphate concentrations and baclofen concentrations are presented in FIGS. 20-21. Results of the levels of 4-CCP observed at various sulfate concentrations and baclofen concentrations are presented in FIG. 22. These results represent 9 weeks at 37° C. Similar results are presented in the bar graph in FIG. 23.

Figure 24:
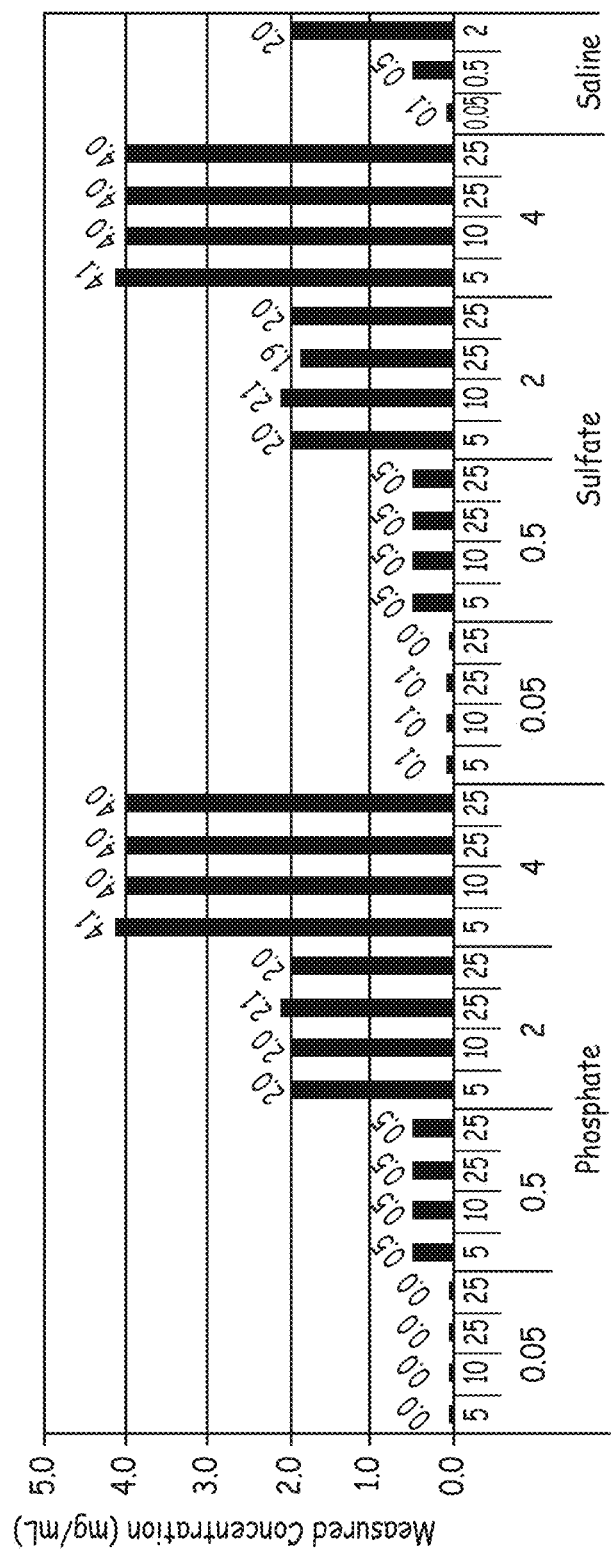

Results at 9 weeks at ambient temperature are shown in FIG. 24.

Conclusions from this study are as follows:
1. No precipitation or particulates observed for all formulations (even at 4° C.) up to 9 weeks
2. pH range is within 6-8, compatible with CSF
3. Impurity level consistent with or better than Lioresal® formulations
4. Higher baclofen solubility (≥4 mg/mL) than Lioresal® (2 mg/mL) is achieved
5. Phosphate and sulfate are compatible with CSF Table 10 below provides some examples of suitable formulations for high concentration baclofen (>2 mg/mL).

TABLE 10

Examples of Suitable Baclofen Formulations
Baclofen Formulations

| | | |
| --- | --- | --- |
| Sulfate | 5 mM $Na_2SO_4$, pH 6 | Add NaCl to 0.154 Molarity |
| | 10 mM $Na_2SO_4$, pH 6 | |
| | 25 mM $Na_2SO_4$, pH 6 | |
| | 25 mM $Na_2SO_4$, pH 6 | No NaCl |
| Phosphate | 5 mM $NaH_2PO_4$, pH 6 | Add NaCl to 0.154 Molarity |
| | 10 mM $NaH_2PO_4$, pH 6 | |
| | 25 mM $NaH_2PO_4$, pH 6 | |
| | 25 mM $NaH_2PO_4$, pH 6 | No NaCl |

It is noted that the pH of formulations with phosphate do not shift as much after sterilization as sulfate formulations. However, at lower concentrations, a bit more 4-CPP is generated with phosphate formulations relative to sulfate formulations.

Thus, embodiments of BACLOFEN FORMULATION FOR USE IN IMPLANTABLE INFUSION DEVICES are described. It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An injectable baclofen solution, the solution comprising: baclofen in a concentration greater than 2 mg/mL; sulfate or phosphate in a concentration of between 10 mM and 25 mM, wherein the solution has an ionic strength equivalent of between 1, the solution c.4 M NaCl and 1.6 M NaCl comprising less than 1.3% of 4-(4-chlorophenyl)-2-pyrrolidinone (4-CPP) after at least 30 days of storage at room temperature, wherein the solution has a pH between about 5.5 and 6.5.

2. The injectable solution of claim 1, wherein solution is sterilized and comprises 0.2% to 1.1% of 4-(4-chlorophenyl)-2-pyrrolidinone (4-CPP) after at least 30 days of storage at room temperature.

3. The injectable solution of claim 1, wherein the solution is sterilized and comprises 0.2% to 1.1% of 4-(4-chlorophenyl)-2-pyrrolidinone (4-CPP) after at least 6 months of storage at room temperature.

4. The injectable solution of claim 1, wherein the solution comprises 0.2% to 0.4% of 4-(4-chlorophenyl)-2-pyrrolidinone (4-CPP) after at least 6 months of storage at room temperature.

5. The injectable solution of claim 1, wherein the baclofen is at a concentration between 2.1 mg/mL and 7 mg/mL.

6. The injectable solution of claim 1, wherein the solution consists essentially of the baclofen, the sulfate or phosphate, sodium ion, and water.

7. The injectable solution of claim 1, further comprising NaCl, wherein the NaCl is present in an amount to provide the solution with an ionic strength equivalent to 1.5 M NaCl.

8. The injectable solution of claim 7, wherein the solution consists essentially of the baclofen, the sulfate or phosphate, sodium ion, chloride ion, and water.

9. The injectable solution of claim 1, wherein the sulfate is derived from $Na_2SO_4$.

10. The injectable solution of claim 1, wherein the phosphate is derived from $NaH_2PO_4$.

11. The injectable solution of claim 1, wherein the solution has a pH of 6.0.

12. The injectable solution of claim 1, wherein the solution comprises 0.2% to 0.4% of 4-(4-chlorophenyl)-2-pyrrolidinone (4-CPP) after at least 30 days of storage at room temperature.

13. A method for preparing an injectable baclofen solution of claim 1, the method comprising:
    dissolving baclofen in aqueous solvent, selected from water, a saline solution, water containing phosphate or sulfate, or a saline solution containing sulfate or phosphate, to generate an initial solution
    adjusting the pH of the initial solution to between 5.5 and 6.2 to produce a pH adjusted solution; and
    steam sterilizing the pH adjusted solution to achieve a sterility assurance level of $1\times10^6$, producing a the injectable baclofen solution.

14. The method of claim 13, wherein the steam sterilizing comprises sterilizing to an F° for at least 15 minutes at 121° C.

15. The method of claim 13, wherein the terminally sterilized solution, after storage of 6 months at room temperature, has a pH of between 5.5 and 6.2 and has less than 1.3% of 4-CPP.

16. The method of claim 13, wherein the initial solution further comprises NaCl.

17. The method of claim 16, wherein the initial solution comprises NaCl in an amount that provides the initial solution with an ionic strength equivalent to 1.4 M NaCl and 1.6 M NaCl.

18. The method of claim 13, wherein the terminally sterilized solution has less than 1% of 4-(4-chlorophenyl)-2-pyrrolidinone (4-CPP) based on the concentration of baclofen added to the initial solution.

19. The method of claim 13, wherein the terminally sterilized solution, after storage of 6 months at room temperature, has less than 1% of 4-(4-chlorophenyl)-2-pyrrolidinone (4-CPP) based on the concentration of baclofen added to the initial solution.

20. The method of claim 13, wherein the terminally sterilized solution, after storage of 6 months at room temperature, has a pH of between 5.5 and 6.2.

21. The method of claim 13, wherein adjusting the pH of the initial solution comprises adjusting the pH to between 5.5 and 6.0.

22. The method of claim 13, wherein the concentration of baclofen in the initial solution is about 2 mg/mL and wherein adjusting the pH of the initial solution comprises adjusting the pH to between 5.5 and 6.2.

23. The method of claim 13, wherein adjusting the pH of the initial solution comprises adjusting the pH with HCl, $H_2SO_4$, $H_3PO$ or NaOH.

24. A method for preparing solution of claim 1, the method comprising:
    adjusting a pH of baclofen in an aqueous solvent to between about 5.5 to 6.5 to form a pH adjusted solution, the aqueous solvent comprising water, a saline solution, water containing phosphate, sulfate, potassium, magnesium or a saline solution containing sulfate, phosphate, potassium or magnesium; and
    steam sterilizing the pH adjusted solution to achieve a sterility assurance level of $1\times10^6$ so as to form a terminally sterilized solution.

25. The method of claim 24, wherein the terminally sterilized solution comprises about 0.2% to about 1.1% of 4-(4-chlorophenyl)-2-pyrrolidinone (4-CPP) after at least 30 days of storage at room temperature.

26. The method of claim 24, wherein the terminally sterilized solution comprises about 0.2% to about 0.4% of 4-(4-chlorophenyl)-2-pyrrolidinone (4-CPP) after at least 6 months of storage at room temperature.

27. The method of claim 24, wherein the concentration of baclofen in the pH adjusted solution is between 2 mg/mL and 7 mg/mL and the baclofenis D-baclofen.

28. The method of claim 24, wherein the concentration of baclofen in the pH adjusted solution is between 2 mg/mL and 7 mg/mL and the baclofen is DL-baclofen racemate.

29. A method of reducing formation of 4-(4-chlorophenyl)-2-pyrrolidinone (4-CPP) in an injectable baclofen solution of claim 1, the method comprising:
    adjusting a pH of baclofen in an aqueous solvent to between about 5.5 to 6.5 to form a pH adjusted solution, the aqueous solvent comprising water, a saline solution, water containing phosphate, sulfate, potassium, magnesium or a saline solution containing sulfate, phosphate, potassium or magnesium, and
    steam sterilizing the pH adjusted solution to achieve a sterility assurance level of $1\times10^6$ so as to form a terminally sterilized solution.

30. The method of claim 29, wherein the terminally sterilized solution comprises about 0.2% to about 0.8% of 4-(4-chlorophenyl)-2-pyrrolidinone (4-CPP) after at least 30 days of storage at room temperature.

31. The method of claim 29, wherein the terminally sterilized solution comprises about 0.2% to about 0.4% of 4-(4-chlorophenyl)-2-pyrrolidinone (4-CPP) after at least 6 months of storage at room temperature.

32. The method of claim 29, wherein the concentration of baclofen in the pH adjusted solution is between 2 mg/mL and 7 mg/mL and the baclofen is D-baclofen.

33. The method of claim 29, wherein the concentration of baclofen in the pH adjusted solution is between 2 mg/mL and 7 mg/mL and the baclofen is DL-baclofen racemate.

34. An injectable baclofen solution, the solution consisting of:
    baclofen in a concentration greater than 2 mg/mL; sulfate or phosphate in a concentration of between 10 mM and 25 mM, wherein the solution has an ionic strength equivalent of between 1.4 M NaCl and 1.6 M NaCl, the solution comprising less than 1.3% of 4-(4-chlorophenyl)-2-pyrrolidinone (4-CPP) after at least 30 days of storage at room temperature, wherein the solution has a pH between about 5.5 and 6.5.

* * * * *